United States Patent [19]

Ueno

[11] Patent Number: 4,770,633

[45] Date of Patent: Sep. 13, 1988

[54] WAX SHAPING TOOL

[75] Inventor: Masato Ueno, Hiroshima, Japan

[73] Assignee: Molten Corporation, Hiroshima, Japan

[21] Appl. No.: 76,568

[22] Filed: Jul. 22, 1987

[30] Foreign Application Priority Data

| Aug. 6, 1986 [JP] | Japan | 61-184939 |
| Aug. 7, 1986 [JP] | Japan | 61-186163 |
| Nov. 10, 1986 [JP] | Japan | 61-268086 |
| Dec. 17, 1986 [JP] | Japan | 61-300893 |
| Apr. 24, 1987 [JP] | Japan | 62-102848 |
| May 14, 1987 [JP] | Japan | 62-117753 |
| May 25, 1987 [JP] | Japan | 62-78535[U] |

[51] Int. Cl.⁴ ............................................. A61C 3/00
[52] U.S. Cl. .................................... 433/32; 222/146.5
[58] Field of Search ............ 433/32; 222/146.5, 146.2; 219/469, 385

[56] References Cited

U.S. PATENT DOCUMENTS

| 1,880,176 | 9/1932 | Harris | 433/32 |
| 1,905,987 | 4/1933 | Lane | 219/21 |
| 2,055,025 | 9/1936 | Brandenburg | 433/32 |
| 2,097,098 | 10/1937 | Hiscox | 219/21 |
| 2,111,645 | 3/1938 | Slutzky et al. | 433/32 |
| 2,119,908 | 6/1938 | Ellis | 219/21 |
| 2,184,105 | 12/1939 | Steiner | 433/32 |
| 2,243,400 | 5/1941 | Stack | 219/21 |
| 2,468,818 | 5/1949 | Fox et al. | 219/21 |
| 3,204,828 | 9/1965 | Paulsen | 222/146.5 |
| 3,385,954 | 5/1968 | Rabinowitz et al. | 433/32 |
| 3,800,122 | 3/1974 | Farmer | 219/239 |
| 3,902,043 | 8/1975 | Rogan | 219/242 |
| 4,301,357 | 11/1981 | Huffman | 219/229 |
| 4,378,076 | 3/1983 | Stirnweiss | 222/146.5 |

FOREIGN PATENT DOCUMENTS 2539073  7/1984  France .................................. 433/32

Primary Examiner—John J. Wilson
Attorney, Agent, or Firm—Armstrong, Nikaido, Marmelstein & Kubovcik

[57] ABSTRACT

A wax shaping tool comprising a handle portion, a means for slidably supporting wax rod with a stopper at the front end thereof, a forming spatula portion in front of the handle portion for holding and flowing wax, a wax melter provided on the forming spatula portion, a heater, a wax feed controller for controlling the contact of wax rod with the wax melter by means of controlling the movement of the wax rod supporting means and/or wax rod and/or the stopper and/or the wax melter. The tool enables a wax shaping work to be carried out rapidly and efficiently without a fear of wax degradation, or wax rod deformation.

48 Claims, 14 Drawing Sheets

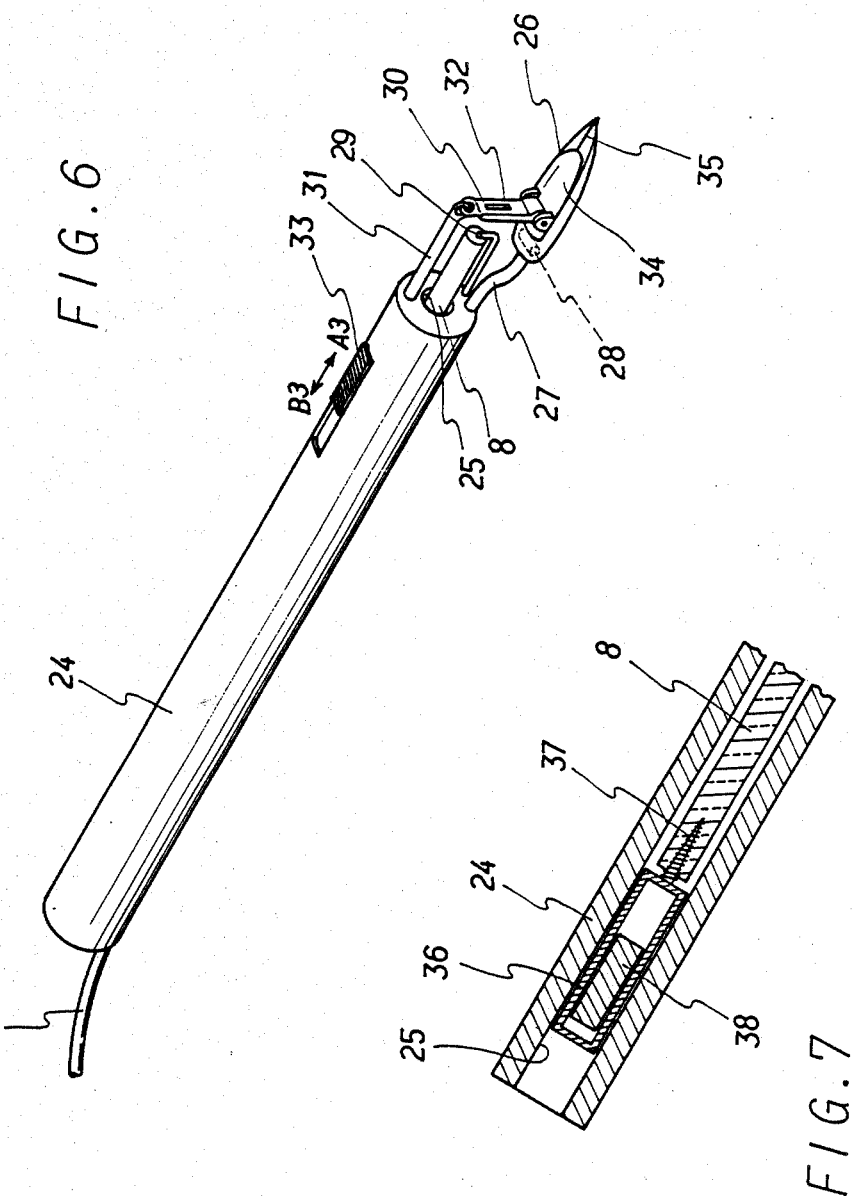

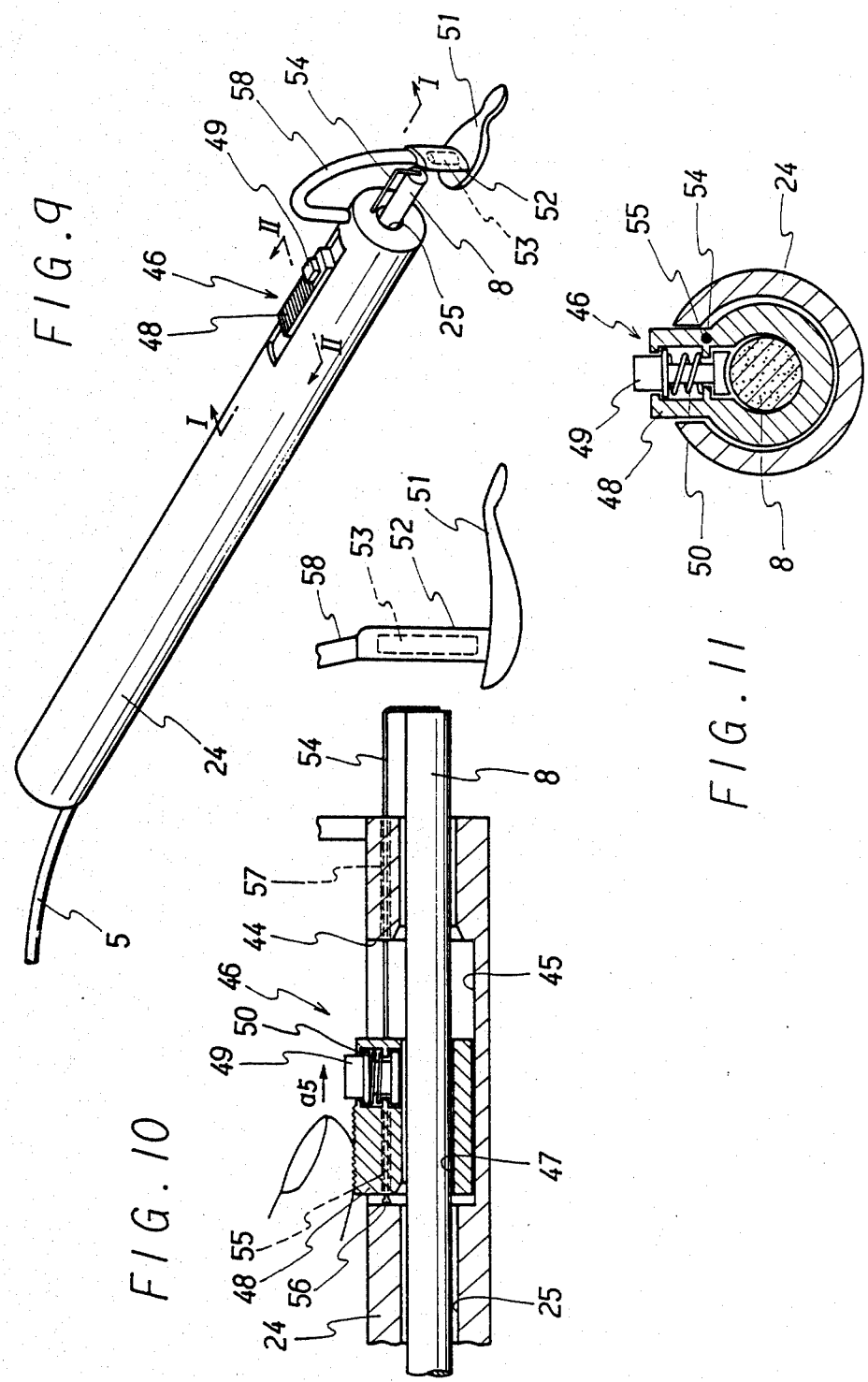

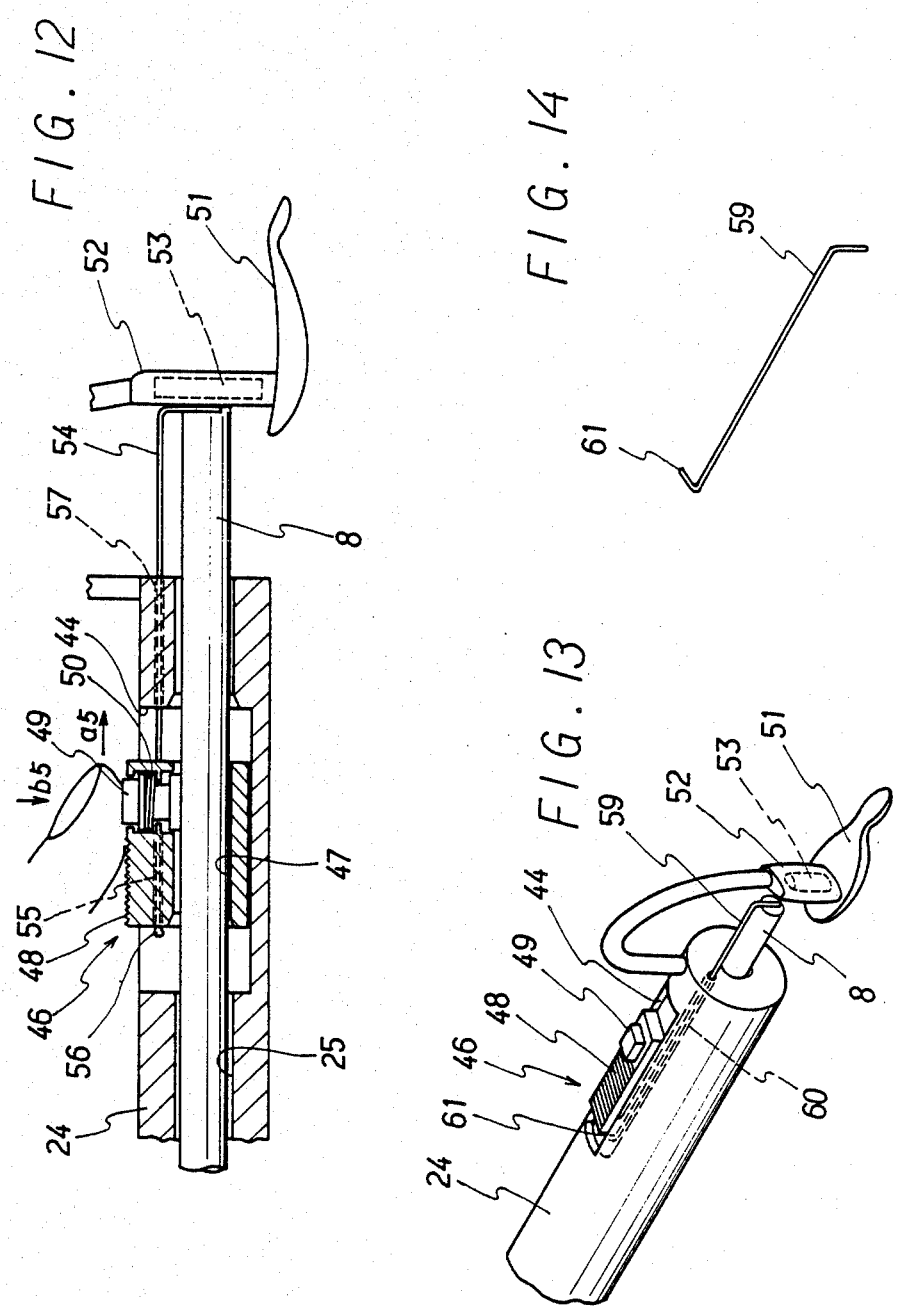

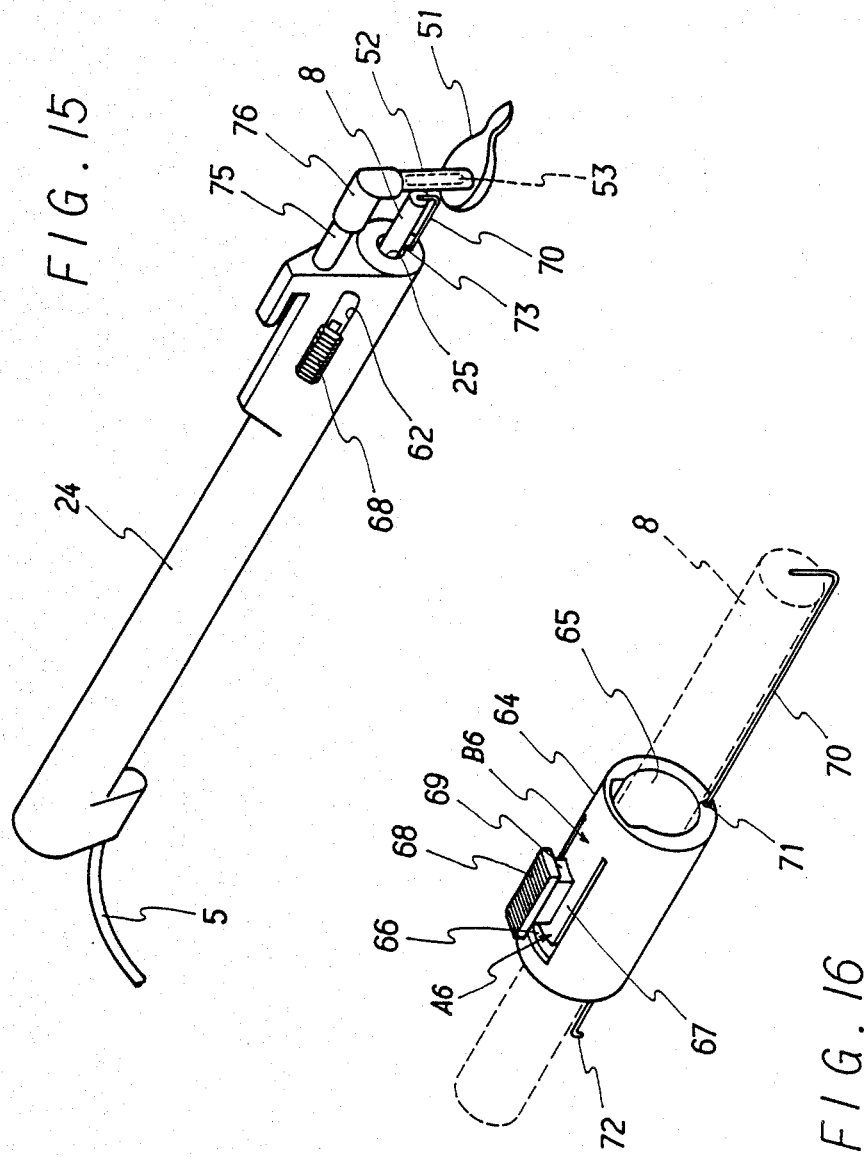

WAX SHAPING TOOL

BACKGROUND OF THE INVENTION

The present invention relates to a wax shaping tool used in forming an artifitial denture model with dental wax on a dental cast obtained from a patient.

In building and shaping of wax in the field of denture work, the following steps are usually repeated more than ten times for one tooth; (a) first to hold wax in the heated spatula by dipping softened or melted solid wax; (b) then to heat it up again to make it in a liquid form; and (c) to build it up at the region where wax shaping is to be performed.

In this conventional procedure, the point of regard of the dental technician moves outside of the region every time the above steps are repeated. Accordingly, it is difficult for the dental technician to concentrate his attention on the wax shaping work, and consequently the efficiency of the work is extremely lowered.

In order to improve the efficiency of the above troublesome work, there has been proposed a construction combining a heater and a spatula and providing direct heating of the spatula by the heater. Examples of such construction can be seen in U.S. Pat. Nos. 1,905,987, 2,097,098, 2,119,908, 2,468,818, 3,800,122, 3,902,043 and 4,301,357.

However, even if a spatula having the above proposed construction is employed, the work includes essentially a step for dipping wax from another place and still requires the dental technician to make his point of regard off the region. Accordingly, the improvement in the efficiency of the work is not satisfactory.

Another example construction of the conventional tool is disclosed in U.S. Pat. No. 2,243,400, wherein a heater and a wax reservoir are provided in a handle portion and stored molten wax is delivered to a spatula formed at the front end portion.

However, since the molten wax is stored in wax reservoir, the above example construction has a drawback that there might occur a degradation of wax or a separation of wax component before the molten wax is delivered to the spatula and as a result the wax might become inadequate for the denture work where a high tolerance is required.

An object of the present invention is to provide a wax shaping tool which allows a dental technician to perform a wax shaping work continuously without making his point of regard off the region to be shaped, and therefore, which enables a wax shaping work to be carried out rapidly and efficiently.

Another object of the present invention is to provide a wax shaping tool wherein solid wax is melted just before a wax shaping work so that the work can be carried out with avoiding the degradation of wax or the separation of wax component.

A further object of the invention is to provide a wax shaping tool wherein a solid wax rod, which is apt to be softened and deformed by an external force, can be fed without being associated with deformation, bending or the like.

BRIEF SUMMARY OF THE INVENTION

In accordance with the present invention there is provided a wax shaping tool comprising:
a handle portion suitable for holding in a hand; a means for supporting wax rod, which is fixed to the handle portion and has a stopper at the front end thereof, wherein a wax rod is supported slidably downward by gravity and stops with the front end thereof abutting against the stopper;
a forming spatula portion made of metalic material and fixed to the front side of the handle portion, which can hold up molten wax and also has a function to flow wax to the region for shaping and to build up and shape wax;
a wax melter made of metalic material and provided on and connected to the forming spatula portion, which can melt the wax rod at contacting surface;
a heater which heats up the forming spatula poriton and the wax melter;
a wax feed controller which makes the front end of the wax rod and the wax melter in contacted condition or in released condition, where in contacted condition the wax rod is melted from the front end then continues to be melted due to sliding down of wax rod by gravity and molten wax accumulates in the forming spatula portion, while in released condition the wax rod stops being melted.

Further in accordance with the present invention there is also provided a wax shaping tool comprising:
a handle portion suitable for holding in a hand;
a means for supporting wax rod comprising first longitudinal bore formed in the handle portion, wherein a wax rod is inserted into the first longitudinal bore and supported slidably downward by gravity;
a forming spatula portion made of metalic material and fixed to the front side of the handle portion, which can hold up molten wax and also has a function to flow wax to the region for shaping and to build up and shape wax;
a wax melter made of metalic material and provided on and connected to the forming spatula portion, which can melt the wax rod at contacting surface;
a heater which heats up the forming spatula portion and the wax melter;
a stopper supported by the handle portion, of which the front end is disposed between the front end of the handle portion and the wax melter, wherein the wax rod inserted in the first longitudinal bore stops with the front end of the wax rod abutting against the front end thereof; and
a wax feed controller which makes the front end of the wax rod and the wax melter in contacted condition or in released condition, where in contacted condition the wax rod is melted from the front end and molten wax accumulates in the forming spatula portion, while in released condition the wax rod stops to be melted, the wax feed controller comprising a first controlling means comprising a means for operating the stopper, which is provided at the handle portion and moves the stopper to a forward position or to a rear position, where in the forward position the stopper contacts the wax melter to allow the wax rod to be melted from the front end and to be continuously melted due to sliding down of the wax rod by gravity and molten wax accumulates in the forming spatula portion, while in the rear position the stopper parts from the wax melter and the front end of the wax rod also parts therefrom; and a second controlling means which can force wax rod to proceed forward and can press the front end of the wax rod against the wax melter when the stopper is in the forward position In this specification, the term "wax shaping" means building up and shaping wax.

BRIEF DESCRIPTION OF THE DRAWING

The features and advantages of the wax shaping tool of the present invention will become more clearly appreciated from the following description in conjunction with the accompanying drawings, in which:

FIG. 6 is a perspective view of the third embodiment of a wax shaping tool in accordance with the present invention;

FIG. 7 is a sectional view of the rear part of the handle portion of the third embodiment in FIG. 6;

FIG. 9 is a perspective view of the fifth embodiment of a wax shaping tool in accordance with the present invention;

FIG. 10 is a sectional view taken along the plane indicated as the line I—I in FIG. 9;

FIG. 11 is a sectional view taken along the plane indicated as the line II—II in FIG. 9;

FIG. 12 is a partially sectional view of the fifth embodiment with the button being pressed;

FIG. 13 is a perspective view of an example of an alternative construction for a stopper arrangement;

FIG. 14 is a perspective view of a stopper used in the example in FIG. 13;

FIG. 15 is a perspective view of the sixth embodiment of a wax shaping tool in accordance with the present invention;

FIG. 16 is a perspective view showing the inner tubular member and the stopper of the six embodiment;

DETAILED DESCRIPTION OF THE INVENTION

First, there is explained the first aspect of the present invention, wherein a wax rod slides down by gravity, referring to the first, the second, the third and the fourth embodiments.

Figure 1:
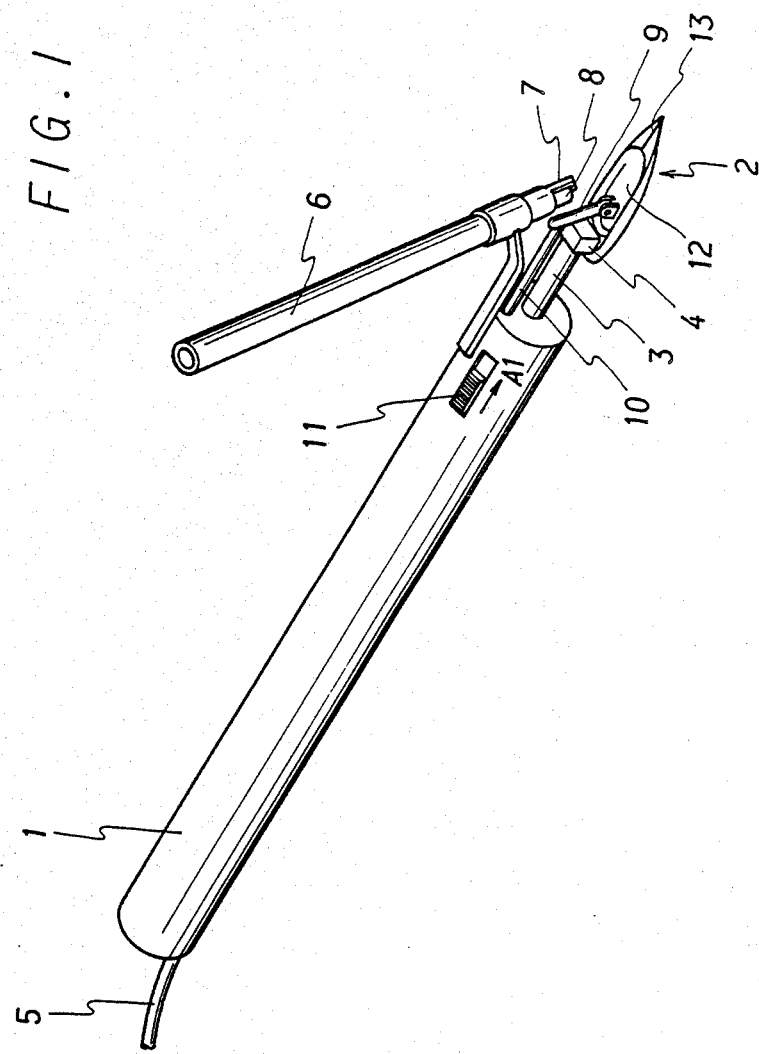
FIG. 1 is a perspective view of the first embodiment of a wax shaping tool in accordance with the present invention.
Figure 2:
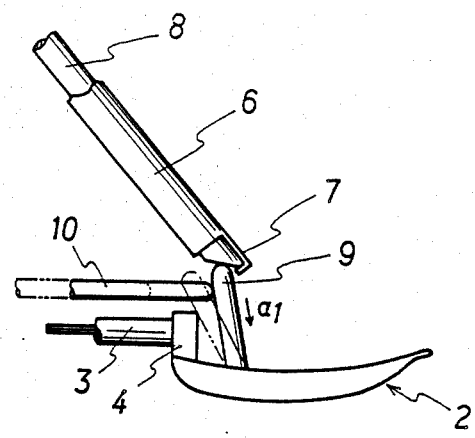
FIG. 2 is a partially side view of the front part of the first embodiment in FIG. 1.
Figure 3:
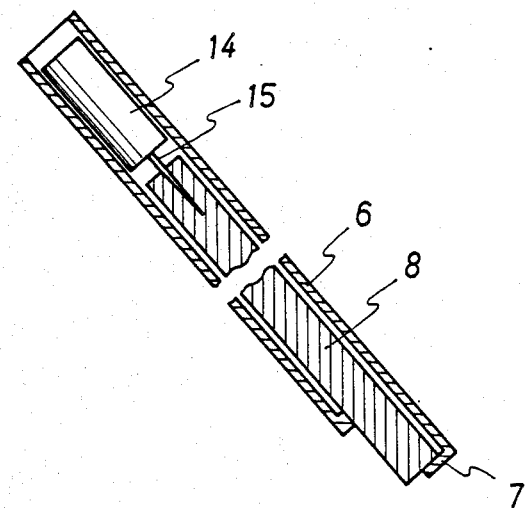
FIG. 3 is a sectional view of a means for supporting wax rod of the first embodiment in FIG. 1.

The first embodiment of the wax shaping tool in accordance with the present invention is illustrated in FIG. 1 to FIG. 3. In those drawings, the numeral 1 is a handle portion, which has an elongated shape like a rod, being formed with plastic material or the like. The numeral 2 is a forming spatula portion like a streamline-shaped dish which is fixed to the edge of the handle portion 1 with an insulator 3 between them. The numeral 4 is a heater formed on the rear side of the forming spatula portion 2. Electric power is supplied by an electric wire 5 laid through the insulator 3 and the handle portion 1. The numeral 6 is a means for supporting wax rod, which is fixed to and supported by the end of the handle portion in such a manner that the lower end of the wax rod supporting means 6 is positioned at about 7 mm above the forming sputula portion 2 and the wax rod supporting means 6 is disposed in inclined direction relative to the handle portion at an angle of about 40 degrees. A transparent pipe of plastics with both ends being opened can be used as the wax rod supporting means 6, so that the consumption of the wax rod can be seen. The numeral 7 is a stopper comprising an L-shaped fine metal thread formed at the lower end of the wax rod supporting means 6. The bent end of the stopper 7 projects toward the center of the opening of the wax rod supporting means 6 and can have a length approximately equal to the radius of the opening. A wax rod 8 is inserted into the wax rod supporting means 6 and is allowed to slide down by gravity and to stop with abutting against the stopper 7.

The wax rod supporting means 6 inclines relative to the longitudinal direction of the handle portion 1 at an angle of about 40 degrees, but any other angle can be selected within the range from about 15 to about 60 degrees. An angle smaller than about 15 degrees is not preferable, because such a small angle will make it difficult to hold the handle portion 1 then the handling of the tool will be inconvenient, and also because such an angle will reduce the resultant force for sliding down by gravity. The maximum value of 60 degrees is selected because the value makes the wax rod supporting means 6 incline at about 90 degrees relative to the horizontal plane, wherein the resultant force for sliding down of wax rod becomes at maximum. This is based on the fact that the wax shaping tool of this kind is held by a hand usually in a position where the handle portion 1 inclines at an angle of about 30 degrees relative to the horizontal plane, when it is used. To increase the angle or to incline outward the wax rod supporting means 6 is not a preferable way because the wax rod supporting means 6 projects too much and disturbs the operation of the tool, and there is a fear of contacting the region for wax shaping, further because the inclining angle of the wax rod supporting means 6 is canceled to the extent corresponding to the inclining angle of the handle portion 1 and the resultant force for sliding down by gravity is reduced. Considering the sliding capability of the wax rod and operability of the tool, preferable range of the angle is from 20 to 40 degrees.

The pipe which forms the wax rod supporting means 6 is required to have an inside diameter larger than the diameter of the wax rod 8 used. When the wax rod 8 having a diameter of 4 mm is used, the inside diameter of the plastic pipe is preferably about 5 mm.

The numeral 9 is a wax melter having a columnar shape, of which one end is mounted on the forming spatula portion 2 rotatively and the other end is free. The wax melter 9 has a length of about 1 cm so that the free end thereof can contact the lower end of the wax rod 8. The numeral 10 is a rod member being supported slidably by the handle portion 1, which serves as a means for operating wax melter. Namely, the front end of the rod member 10 can abuts against the free end of the wax melter 9 to rotate the wax melter 9 so that the free end thereof contacts the lower end of the wax rod 8. The numeral 11 is a slidable button which enables to operate the rod member 10 manually by a finger. These rod member 10 and the slidable button 11 can be equipped with a spring means (not shown in the drawings) so that they can always be urged toward the reverse direction of the arrow A1. The wax melter 9 is arranged so that it rests on the heater 4 by gravity as shown in FIG. 2 when it is not operated by the rod member 10. The wax melter 9 contacts the lower end of the wax rod 8 only when it is pressed by the rod member 10. The wax rod 8 is melted at the part in contact with the heated wax melter 9, and the molten wax flows downward along the wax melter 9 in the direction of the arrow a1. The wax melter 9 can be equipped with a spring means which urges the wax melter 9 toward the heater 4 in order to ensure the wax melter 9 being apart from the lower end of the wax rod 8 when it is not pressed by the rod member 10.

The forming spatula portion 2 and the wax melter 9 are made of metalic material having high thermal conductivity e.g. copper, brass, Ni-Co alloy, Co-Cr alloy or the like. Therefore, the forming spatula portion 2 and the wax melter 9 are easily heated to about 100° C. by the heater 4. The heating temperature of the heater 4 can be set adequately in accordance with the kind of wax material within the range from about 80° to 120° C. The forming spatula portion 2 comprises a wax reservoir 12 for molten wax and a narrow ditch 13 which allows molten wax to flow from the wax reservoir 12 to the front end of the forming spatula portion.

FIG. 3 shows the wax rod supporting means 6 with the wax rod 8 inserted therein. There is formed a play between the inner wall of the pipe forming the wax rod supporting means 6 and the wax rod 8 so that the wax rod 8 can slide down by gravity. The numeral 14 is a columnar wight having a needle 15 extending along the longitudinal central axis, which is fixed to the upper end of the wax rod 8 by inserting the needle 15 into the wax rod 8 at the center of the end plane. The weight 14, which effectivey asists the wax rod 8 to slide down particularly when the wax rod 8 becomes short as a result of consumption and is not able to slide satisfactorily, can be used where necessary. Since the weight 14 is larger than wax rod 8 in outside diameter, to insert the needle 15 to the center of the end plane of the wax rod 8 provides the annular play between the rear portion of the wax rod 8 and the inner wall of the wax rod supporting means 6 so that the wax rod 8 can smoothly slide down in the wax rod supporting means 6.

Figure 4:
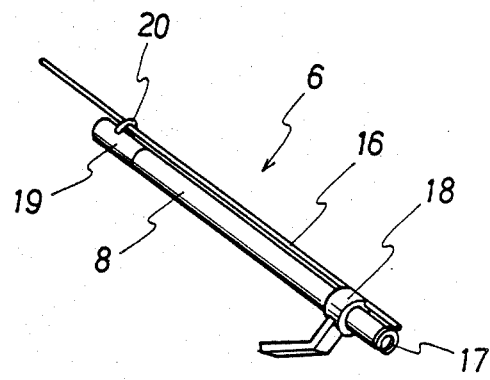
FIG. 4 is a perspective view of another embodiment of a means for supporting wax rod.

The wax rod supporting means 6 in the above embodiment is made of a pipe of plastic material, but the construction illustrated in FIG. 4 can be employed alternatively. In this alternative construction, the wax rod supporting means 6 comprises a slender guide rod 16 made of metalic material or the like, a U-shaped stopper 17 fixed at the lower end of the guide rod 16, a guide ring 18 fitted to the vicinity of the lower end of the guide rod 16 and a cap 19 hung slidably from the guide rod 16. The wax rod supporting means 6 is fixed to the handle portion 1 (FIG. 1) at the guide ring 18. The cap 19 has a ring 20 to be passed through by the guide rod 16 and has a needle (not shown in the drawings) to be inserted into the wax rod 8 at the end plane thereof for the connection of the cap 19 and the wax rod 8. Thus the wax rod 8 is supported in such a manner that the upper end thereof is fitted with the cap 19 which is in turn slidably hung by the guide rod 16 passing through the ring 20, then is stopped sliding down by the stopper 17. The wax melter 9 (FIG. 1) can approach to the wax rod by passing through the opening of the U-shaped stopper 17 in order to melt the lower end of the wax rod 8. The wax rod 8 slides down by gravity while the lower end thereof is melted until the ring 20 of the cap 19 abuts against the guide ring 18 when the consumption of the wax rod ceases.

When the above described tool is used, the slidable button 10 is slided by finger in the direction of the arrow A1 after heating up the forming spatula portion 2 and the wax melter 9 by means of the heater 4. Thereby, the rod member 10 abuts against the free end of the wax melter 9 and pushes to rotate it. The rotated wax melter 9 contacts the lower end of the wax rod 8 and melts it. The molten wax flows down in the direction of the arrow a1 along the wax melter 9 and accumulates in the wax reservoir 12 of the forming spatula portion 2. Then the molten wax is poured to the region for wax shaping. When molten wax is poured to periphery of crown, occlusal surface or the like, molten wax is poured form the side of the forming spatula portion 2. On the contrary, when a delicate wax shaping work such as forming work of a cusp is carried out, molten wax is poured from the end of the forming spatula portion 2 via the narrow ditch 13.

Figure 5:
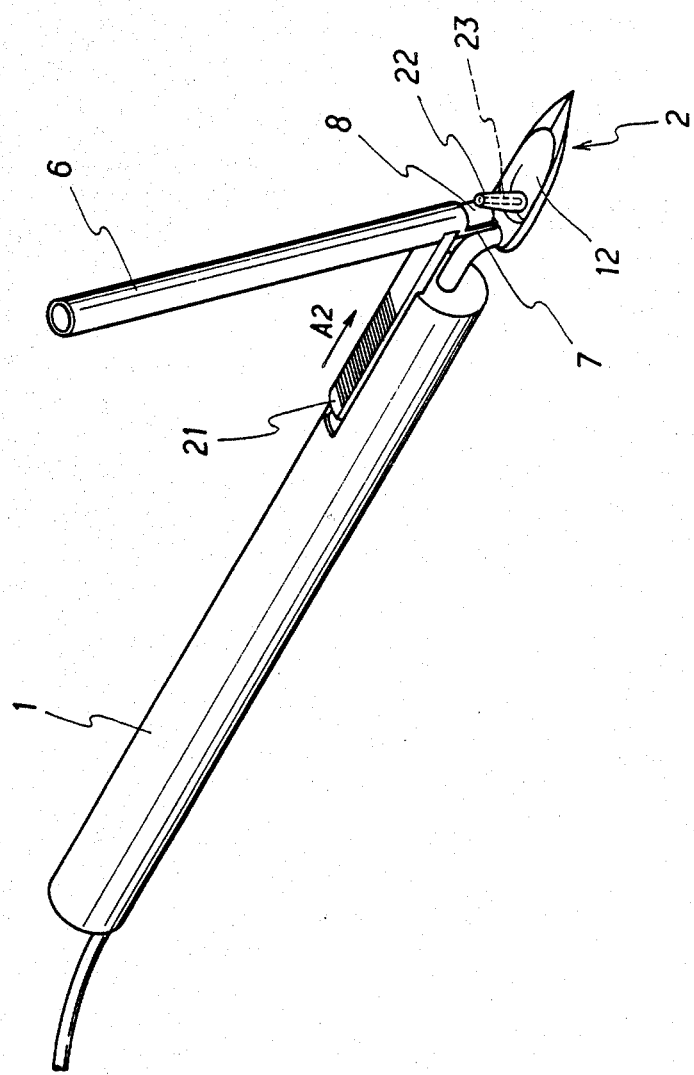
FIG. 5 is a perspective view of the second embodiment of a wax shaping tool in accordance with the present invention.

The second embodiment of the wax shaping tool in accordance with the present invention is illustrated in FIG. 5.

In FIG. 5, a wax rod supporting means 6 is mounted slidably on a handle portion 1. Namely, the wax rod supporting means 6 can move forward and backward on the handle portion 1 at the connecting area, and this movement can be controlled by a slidable button 21. The wax rod supporting means 6 and the slidable button 21 organize a means for controlling wax feed. A wax melter 22 is fixed on a forming spatula portion 2, and a heater 23 is embedded in the wax melter 22. The heater 23 can be located at the rear part of the forming spatula portion 2 like the heater 4 in the first embodiment or at other proper position. The heater 23 heats up the forming spatula portion 2 and the wax melter 22 like the previously mentioned one. A stopper 7 is provided at the lower end of the wax rod supporting means 6 on the side near the handle portion 1. Excepting the above, the second embodiment has the similar construction to the first embodiment.

In the second embodiment, when the slidable button 21 is moved in the direction of the arrow A2, the wax rod supporting means 6 is moved forward and the lower end of the wax rod 8 is brought in contact with the heated wax melter 22. Thereby, the wax rod is melt at the lower end, and molten wax flows down along the wax melter 22 and accumulates in the wax reservoir 12 in the forming spatula portion 2. The amount of molten wax can be controlled by the duration time of pressing forward the wax rod supporting means 6. Therefore, when the required amount of molten wax is obtained, the slidable button 21 is moved in the reverse direction of the arrow A2 in order to release the wax rod supporting means 6 from the wax melter 22.

The handle portion 1 can be provided with a spring means in such a manner that the slidable button 21 is always urged in the reverse direction of the arrow A2. When that provision is employed, the wax rod supporting means 6 can be kept apart from the wax melter 22 during non-operating condition and can be moved backward automatically to be returned to non-operating condition when finger is released from the slidable button 21 after pressing in the direction of the arrow A2 for some period, consequently the operability of the tool is further improved.

In the above embodiment, there can be employed an alternative construction wherein the slidable button 21 with associated parts is formed inside of the handle portion 1 and there is provided a roller contacting the slidable button 21, the rolling of which causes the movement of the slidable button 21. Thereby, to rotate the roller by finger in the backward direction or in pulling direction (in the reverse direction of the arrow A2) makes the wax rod supporting means 6 move forward. This alternative construction is effective considering the fact that it is easier to bend a finger than to stretch the same.

Each of the wax sliding tools in accordance with the two embodiments described hereinbefore has the construction, wherein there is formed a separate means for supporting the wax rod in inclined posture outside of the handle portion. The wax rod is supported and allowed to slide down by gravity. The wax rod is contacted and melted at the lower end by the wax melter in accordance with the requirement, and slide down automatically by gravity in the wax rod supporting means in accordance with the consumption. The lower end of the wax rod is always located at the lower end of the wax rod supporting means, where the wax melter can approach.

By virtue of this construction, required amount of molten wax can be flowed down to and accumulted in the forming spatula portion only by the finger operation. Because of this advantage, a dental technician is allowed to carry out a multiplicity of wax shaping operations continuously and concentratively without putting his point of regard off the region for wax shaping. Consequently the efficiency of the denture work is considerably improved.

Further, since no external force to deform the wax rod is added in the above construction, the straight columnar shape of the wax rod can be maintained even in the condition wherein the wax rod is softened due to conducted heat and radiated heat from the heater or due to the room temperature. The fact ensures smooth sliding down and moving of the wax rod in the wax rod supporting means, and enables rapid wax melting.

In the denture works, wax is used as a material for complicated and delicate shaping such as odontogenesis, and the composition thereof is usually conditioned so that the wax can have hardenability and hardening rate optimized suitably for the denture works and can be free from shrinking or deforming after the hardening. Since such type of wax is prepared by blending of two or more kinds of waxes or other components, there is a drawback that separation of some components, decomposition and degradation begin to take place partially just after being melted. Therefore, when the wax which have been once melted is left for a long time, the wax become unsuitable for using in complicated and delicate shaping works like denture works. By virtue of the construction in accordance with the present invention, wax melting is carried out just before the forming work so that the wax can be used in the most preferable condition without any fear of decomposition or degradation.

The third embodiment of the wax shaping tool in accordance with the present invention is illustrated in FIG. 6 and FIG. 7. In these drawing, the numeral 24 is a handle portion, which has a long and slender shape like a rod and has a longitudinal bore 25, being formed with plastic material or the like. The longitudinal bore 25 serves as a wax rod supporting means. The numeral 26 is a forming spatula portion having a shape like a streamline shaped dish, which is fixed to the edge of the handle portion 24 with an insulator 27 between them. The numeral 28 is a heater formed at the rear part of the forming spatula portion 26. Electric power is supplied by an electric wire 5 laid through the insulator 27 and the handle portion 24. The numeral 29 is a stopper comprising an L-shaped fine metal thread provided at the front end of the handle portion 24. The bent end of the stopper 29 may have a length approximately equal to the radius of a wax rod. A wax rod 8 is inserted into the longitudinal bore 25. The wax rod 8 is allowed to slide down by gravity and to stop with abutting against the stopper 29 when the handle portion is held in the inclined posture with the rear end up. The longitudinal bore 25 is required to have an inside diameter larger than the diameter of the wax rod 8 used. When the wax rod having a diameter of 4 mm is used, the inside diameter of the longitudinal bore 25 is preferably about 5 mm to 7 mm.

The numeral 30 is a wax melter having a columnar shape, of which one end is mounted on the forming spatula portion 26 pivotably while the other end is free. The free end of the wax melter 30 projects toward the extended axis of the wax rod 8 along which the wax rod 8 slides down. The wax melter 30 has a length of about 1 cm. The numeral 31 is a rod member being supported slidably by the handle portion 24, which serves as a means for operating wax melter. Namely, the front end of the rod member 31 is connected to the free end of the wax melter 30 to rotate the wax melter 30 so that the free end thereof can contact the front end of the wax rod 8. The numeral 32 is a slit provided in the wax melter 30 to allow the stopper 29 to penetrate thereinto when the wax melter 30 is tilted toward the handle portion 24. To allow the stopper 29 to penetrate into the slit 32 ensures the full contact of the wax rod 8 with the wax melter 30. The numeral 33 is a slidable button which enables to operate the rod member 31 manually by a finger. These rod member 31 and slidable button 33 can be equipped with a spring means (not shown in the drawings) so that they can always be urged toward the direction of the arrow A3. When the slidable button 33 is pressed in the direction of the arrow A3, the wax melter 30 becomes apart from the end of the wax rod 8 as shown in FIG. 6. On the contrary, when the slidable button is moved in the direction of the arrow B3, the wax melter 30 is brought in contact with the end of the wax rod 8. The wax rod 8 is melted at the part in contact with the heated wax melter 30, and molten wax flows downward along the wax melter 30.

The forming spatula portion 26 and the wax melter 30 are made of metalic material having high thermal conductivity like the material used in the first embodiment. Therefore, the forming spatula portion 26 and the wax melter 30 is easily heated to about 100° C. by the heater 28. The heating temperature of the heater 28 can be set adequately in accordance with the kind of wax material in the range from about 80° C. to 120° C. The forming spatula portion 26 comprises a wax reservoir 34 for molten wax and a narrow ditch 34 which allows molten wax to flow from the wax reservoir 34 to the front end of the forming spatula portion.

FIG. 7 shows the handle portion 24 with the wax rod 8 inserted therein. There is formed a play between the inner wall of the longitudinal bore 25 and the wax rod 8 so that the wax rod 8 can slide down by gravity. The numeral 36 is a columnar weight having a screw shaped needle 37 extending along the longitudinal central axis, which is fixed to the rear end of the wax rod 8 by inserting the needle 37 into the wax rod 8 at the center of the end plane. The numeral 38 is a core weight housed slidably along the longitudinal axis in the weight 36. When the core weight 38 falls within the weight 36 and collides with the front end of the weight 36, the impact is transmitted to the wax rod 8. Thereby, driving force for sliding down of the wax rod 8 is increased. The weight 36 is particularly effective when the wax rod 8 becomes short as a result of being consumed and is not able to slide down satisfactorily. When the weight 36 is larger than the wax rod 8 in outside diameter, to insert the needle 37 to the center of the end plane of the wax rod 8 provides the annular play between the wax rod 8 and the inner wall of the longitudinal bore 25 at the rear portion thereof so that the wax rod 8 can smoothly slide down in the longitudinal bore 25.

When the above mentioned tool is used, the handle portion 24 is held in inclined posture (or vertical posture) with the rear end up to make the wax rod 8 slide down and to make the front end thereof abut again the stopper 29. Then the slidable button 33 is slided by finger in the direction of the arrow B3 after heating up the forming spatula portion 27 and the wax melter 30 by means of the heater 28. Thereby, the wax melter 30 rotates toward the handle portion 24 and contacts the end of the wax rod 8 to melt it. Molten wax flows down along the wax melter 30 and accumulates in the wax reservoir 34 of the forming spatula portion 26. Then molten wax is poured to the region to be wax-formed. When molten wax is poured to the periphery of crown, occlusal surface or the like, molten wax is poured from the side of the forming spatula portion 26. On the contrary, when a dilicate wax shaping work such as forming work of a cusp is carried out, molten wax is poured from the end of the forming spatula portion 26 via narrow ditch 35 and the end portion is used for the work.

Figure 8:
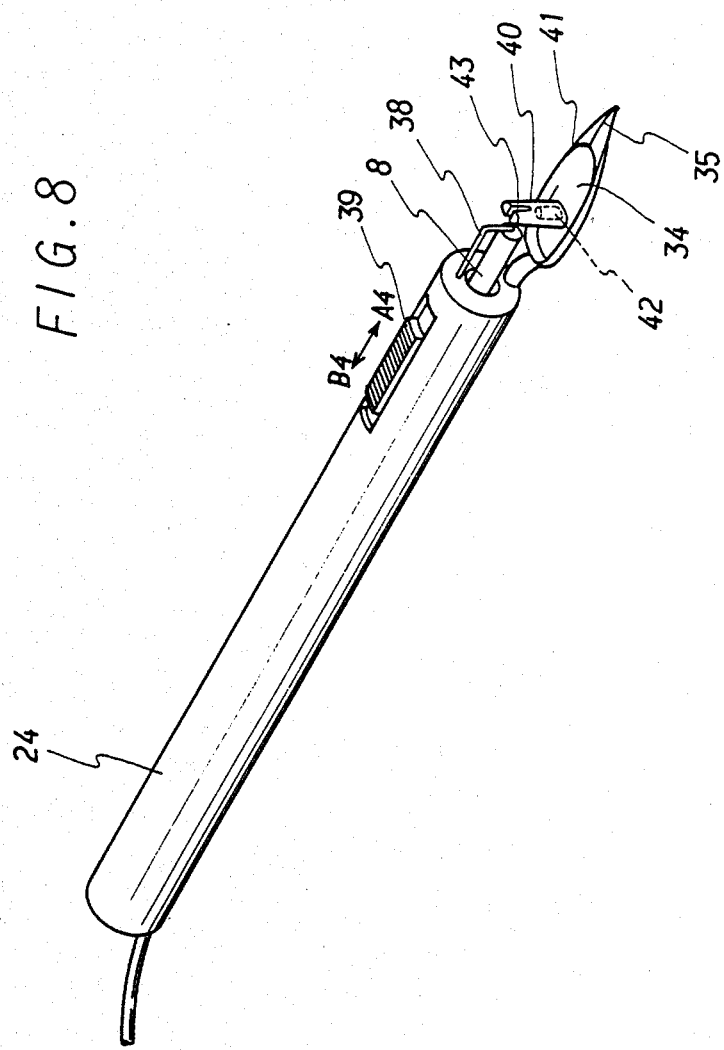
FIG. 8 is a perspective view of the fourth embodiment of a wax shaping tool in accordance with the present invention.

The fourth embodiment of the wax shaping tool in accordance with the present invention is illustrated in FIG. 8.

In FIG. 8, a stopper 38 is mounted slidably on a handle portion 24. Namely, the stopper 38 can move forward and backward in the connecting arrangement with the handle portion 24, and this movement can be controlled by a slidable button 39. The slidable button 39 and the stopper 38 organize a means for controlling wax feed. A wax melter 40 is fixed on the forming spatula portion 41, and a heater 42 is embedded in the wax melter 40. The heater 42 can be located at the rear part of the forming spatula portion 41 like the heater in the third embodiment or at other proper position. The numeral 43 is a slit provided at the upper end of the wax melter 40 and has the similar function to the slit 32 in the third embodiment. Namely, the slit 43 allows the stopper 38 to pass through and ensures the contact of the end of the wax rod 8 with the wax melter 40, when the stopper is moved forward. The heater 42 heats up the forming spatula portion 41 and the wax melter 40 like the previously mentioned one. Excepting those, the fourth embodiment has the similar construction to the third embodiment.

In the fourth embodiment, when the slidable button 39 is moved in the direction of the arrow A4, the stopper 38 is moved forward and the front end of the wax rod 8 is brought into contact with the hot wax melter 40. Thereby, the wax rod 8 is melted at the front end, and molten wax flows down along the wax melter 40 and accumulates in the wax reservoir 34 in the forming spatula portion 41. The amount of molten wax can be controlled by the duration time of pressing forward the stopper 38. Therefore, when the required amount of molten wax is obtained, the slidable button 39 is moved in the direction of the arrow B4 in order to release the stopper 38 from the wax melter 40.

The handle portion 24 can be provided with a spring means in such a manner that the slidable button 39 is always urged in the direction of B4. When that provision is employed, the stopper 38 can be kept apart from the wax melter 40 during non-operating condition and can be moved backward automatically to be returned to the non-operating position when finger is released from the slidable button 39 after pressing in the direction of the arrow A4 for some period, consequently the operability of the tool is further improved.

In the above tool, when the stopper 38 is moved backward to release the wax rod 8 from the wax melter 40 after the melting operation with the wax rod 8 contacting the wax melter 40, the stopper 38 is in embedded condition in the front part of the wax rod 8. At that time the wax rod 8 is fixed to the stopper 38. Therefore, the wax rod 8 does not fall off from the rear end of the handle portion 24 even if the tool is inclined backward. Further, since the wax rod 8 is supported at the end by the stopper 38, there is no fear that the heat radiation from the wax melter 40 and from the forming spatula portion softens to bend downward the wax rod 8.

In the fourth embodiment, there can be employed an alternative construction wherein the slidable button 39 with associated parts is formed inside of the handle portion 24 and there is provided a roller contacting the slidable button 39, the rolling of which causes the movement of the slidable button 39. Thereby, to rotate the roller by finger in the pulling direction (in the direction of the arrow B4 in FIG. 8) makes the stopper 38 move forward. This alternative construction is effective considering the fact that it is easier to bend a finger than to stretch a finger.

The wax shaping tools in accordance with the third and the fourth embodiments described above have the advantageous features similar to that described in the first and the second embodiments.

Next, there is explained the second aspect of the present invention, wherein a wax rod not only slides by gravity but also can be moved manually, referring to the fifth, the sixth and the seventh embodiments.

The fifth embodiment of the wax shaping tool in accordance with the present invention is illustrated in FIG. 9 to FIG. 12. In these drawings, the numeral 24 is a handle portion, which has a long and slender shape like a rod and has a first longitudinal bore 25, being made of plastic material or the like. The first longitudinal bore 25 serves as a wax rod supporting means. The numeral 44 is a first opening of the first longitudinal bore 25 provided near the front end of the handle portion 24. The numeral 45 is a partially expanded bore of the first longitudinal bore 25 provided at the location of the first opening 44.

The numeral 46 is a wax feed controller comprising an inner tubular member housed in the partially expanded bore 45, having a second longitudinal bore 47 along the longitudinal central axis of the handle portion 24 and a slidable button 48 which is passed through the first opening 44 and is exposed at the surface of the handle portion 24. The partially expanded bore 45 extends longer than the wax feed controller 46, and the first opening 44 extends longer than the slidable button 48. Therefore the wax feed controller 46 can be slided forward and backward within the partially expanded bore 45 and the first opening 44. Inside diameter of the second longitudinal bore 47 is equal to or slightly smaller than that of the first longitudinal bore 25. The numeral 8 is a wax rod inserted into both the first and the second longitudinal bore 25, 47, which has a diameter slightly smaller than the inside diameter of the second longitudinal bore 47.

The numeral 49 is a pressing member mounted on the wax feed controller 46 and formed in such a manner that the top surface projects slightly from the surface of the wax feed controller 46 or from the surface of the slidable button 48, while the bottom surface looks out on the second longitudinal bore 47. The pressing member 49 is supported movable upward and downward within the required range (about 2 mm) in the wax feed controller 46, always being urged elastically upward by a spring 50. When the pressing member 49 is not pressed downward, the bottom surface thereof does not project into the second longitudinal bore 47 as shown in FIG. 11. On the contrary, when the pressing member 49 is pressed downward, the bottom surface thereof projects into the second longitudinal bore 47. By the projection of the pressing member 49 into the second longitudinal bore 47, the wax rod 8 is nipped between the bottom surface of the pressing member 49 and the inner bottom surface of the second longitudinal bore 47. Preferably, the bottom surface of the pressing member 49 is made of rubber material to become resilient and is shaped to have a round concave section to fit the wax rod 8.

The numeral 51 is a forming spatula portion being located in front of the handle portion 24 and having a shape like a dish. The numeral 52 is a wax melter, of which one end is mounted on the forming spatula portion 51. The other end of the wax melter 52 projects towards the extended axis along which the wax rod 8 slide down.

The wax melter 52 and the forming spatula portion 51 are integratedly formed with metalic material having high thermal conductivity e.g. copper, brass, Ni-Co alloy, Co-Cr alloy or the like. The numeral 53 is a heater embedded in the wax melter 52 and can be a ceramic heater or the like. By the heater 53, the forming spatula portion 51 and the wax melter 52 is heated to about 100° C.

The numeral 54 is a stopper comprising a nearly L-shaped metal thread and having a hooking means 56 at the rear end thereof. The stopper 54 is supported slidably forward and backward in a small hole 55 provided in the wax feed controller 46, with the front part passing through a small hole 57 provided in the handle portion 24 to project forward from the handle portion 24. The front end of the stopper 54 receives the front end of the wax rod 8 at the location between the handle portion 24 and the wax melter 52 to stop the wax rod 8 from sliding down further.

The slidable button 48 serves as a means for operating the stopper and organizes a first controlling means of the wax feed controller 46. On the other hand, the pressing member 49 organizes a second controlling means of the wax feed controller 46.

The numeral 58 is a heat radiating tube made of metal having high strength such as stainless steel, of which one end is fixed at the front end of the handle portion 24 while the other end is fixed on the top of the wax melter 52 and the middle portion is bowed in reversed U shape. Lead wires (not shown in the drawings) are housed in the heat radiating tube 58 to supply electric power to the heater 53. The lead wires are laid through the handle portion 24 and connected to the electric wire 5.

Next there is explained the use of the tool in accordance with the fifth embodiment. The wax rod 8 is inserted into the first longitudinal bore 25 from the rear end, with the slidable button 48 being in rear position as shown in FIG. 10. When the handle portion 24 is held in inclined or vertical posture with the rear end up, the wax rod 8 slides down by gravity through the second longitudinal bore 47 passing through the first longitudinal bore 25, until the front end thereof abuts against the stopper 54 to stop. At this moment, the stopper 54 is apart from the wax melter 52, and wax melting is not achieved. When the slidable button 48 is pressed to move the wax feed controller 46 forward, the stopper 54 also proceeds due to the weight of the wax rod 8 to become in contact with the wax melter 52. FIG. 12 illustrates the above condition. Then wax melting is commenced.

Molten wax flows down along the wax melter 52 and accumulates in the forming spatula portion 51. The wax rod 8 slides down by gravity according to the consumption, and the front end thereof is always received by the end of the stopper 54. A columnar weight having a diameter almost same as the wax rod 8 can be attached to the rear end of the wax rod 8 in order to help the sliding movement of the wax rod 8 by virtue of the weight.

When the required amount of molten wax is obtained in the forming spatula portion 51, the slidable button 48 is moved backward. Thereby, the stopper 54 and the wax rod 8 are moved backward and the wax rod 8 is released from the wax melter 52. Molten wax accumulated in the forming spatula portion 51 is poured to the region to be wax-shaped and wax shaping work of artificial denture model is carried out.

In wax shaping work, when it is required to melt a lot of wax rapidly, the tool is operated as described below. The slidable button is urged forward with the pressing member 49 being pressed down (the arrow b5) in the condiion that the stopper 54 is in contact with the wax melter 52 as shown in FIG. 12. Thereby, the wax rod 8, being nipped between the pressing member 49 and the wax feed controller 46, is urged forward and is pressed on the wax melter 52. Accordingly, the wax melting rate is increased rapidly.

After the above operation, when the slidable button 48 is moved backward with the pressing member 49 being pushed down, the wax rod 8 is moved backward and the wax melting operation is ceased. When the slidable button 48 is further moved backward, the rear end of the slidable button 48 catches the hooking means 56 provided at the rear end of the stopper 54 and the stopper 54 is moved back. Thus the tool is returned to the initial condition shown in FIG. 10.

FIG. 13 and FIG. 14 show an example of an alternative construction for mounting a stopper 59. In this example, the stopper 59 is supported only by the handle portion 24 slidably forward and backward. Namely, the stopper 59 is inserted into a hole 60 provided adjacent to the first opening 44 in the handle portion 24, and only a hooking means 61 at the rear and thereof projects into the first opening 44 so that the rear end of the slidable button 48 can catch it. In the above construction, when the slidable button 48 is moved forward from the rearmost position in the first opening 44, the stopper slides down forward due to the sliding motion of the wax rod 8 by gravity until the front end thereof abuts against the wax melter 52 to stop. After that, when the slidable button 48 is further urged forward with the pressing member 49 being pressed, the wax rod 8 is pressed on the wax melter 52 by force.

In this operation, the hooking means 61 of the stopper 59 is released from the rear end of the slidable button 48. Therefore, the stopper 59 is not affected by the operation of the slidable button 48.

In case of the previously mentioned fifth embodiment, the stopper 59 passes through not only the handle portion 24 but also the wax feed controller 46. Therefore, if the stopper 59 has a slightly bowed part, the part contacts the inner wall of the small hole 55 and there is a fear that the operation of the wax feed controller 46 is disturbed. However, in case of this example there is no fear like that because the stopper is not supported by the wax feed controller 46.

By employing the construction in accordance with the fifth embodiment, in the usual wax shaping work, the wax rod 8 slides down by gravity until it abuts against the stopper 54, 59 to stop. Accordingly required amount of wax can be easily melted by moving the slidable button 48 forward or backward to make the end of the stopper 54, 59 in contact with or apart from the max melter 52. No deforming external force is added to the wax rod 8. Therefore even when the wax rod becomes deformeable easily due to softening by the conducting heat and radiating heat from the heater or by the room temperature, the wax rod 8 maintains its original straight columnar shape. Consequently the wax rod 8 smoothly slides down in the first and the second longitudinal bore, and wax melting operation can be achieved rapidly.

By employing the above construction, more rapid wax melting is also possible as described below. When the more rapid wax melting is required, the pressing member 49 provided in the wax feed controller 46 is pressed to nip the wax rod 8 between the bottom surface thereof and inner surface of the second longitudinal bore 47 in the wax feed controller 46. Then the wax rod 8 is moved forward together with the wax feed controller 46. Accordingly, the external force to the wax rod 8 is minimized, and the wax rod can be moved with the minimum possibility of deformation.

The sixth embodiment of the wax shaping tool in accordance with the present invention is illustrated in FIG. 15 to FIG. 18. In these drawings, the numeral 24 is a handle portion, which has a long and slender shape like a rod and has a first longitudinal bore 25, being made of plastic material or the like. The first longitudinal bore 25 serves as a wax rod supporting means. The numeral 62 is an opening of the first logitudinal bore 25 provided near the front end of the handle portion 24. The numeral 63 is a partially expanded bore of the first longitudinal bore 25 provided at the location of the opening 62. The numeral 64 is an inner tubular member housed in the partially expanded bore 63, having a second longitudinal bore 65 along the longitudinal central axis of the handle portion 24 and having a U-shaped cutting 66. By the U-shaped cutting 66, a plate spring member 67 is formed on the wall of the inner tubular member 64. A free end A6 of the plate spring member 67 is provided on the rear side of the handle portion 24 relative to a cantilever supporting part B6. The numeral 68 is a button fixed on the plate spring member 67 via a connecting member 69, passing through the opening 62 and being exposed at the surface of the handle portion 24. The button 68 serves as a pressing means. The button 68 and the connecting member 69 can be formed integratedly together with the inner tubular member 64 using the same material. The material can be a resilient plastics such as polyacetal.

The numeral 70 is a stopper comprising a nearly L-shaped metal thread and having a hooking means 72 at the rear end thereof. The stopper 70 is supported slidably forward and backward in a small hole 71 provided in the inner tubular member 64, and pass through a small hole 73 provided in the handle portion 24 to project forward from the handle portion 24.

The partially expanded bore 63 extends longer than the inner tubular member 64 and therefore, the inner tubular member 64 can be slided forward and backward within the partially expanded bore 63 when operated by the button 68. Inside diameter of the second longitudinal bore 65 is equal to or slightly smaller than that of the first longitudinal bore 25.

The numeral 74 is a guide ditch for receiving the lower end of the hooking means 72 provided at the rear end of the stopper 70. By virtue of that, the undesirable rotation of the stopper is prevented.

The inner tubular member 64 serves as a means for operating the stopper. The inner tubular member 64, the plate spring member 67 and the button 68 organize a wax feed controller. Wherein, the inner tubular member 64 corresponds to a first controlling means while the plate spring member 67 and the button 68 which serves as a plate spring pressing member correspond to a second controlling means.

The numeral 8 is a wax rod inserted into both the first and the second longitudinal bore 25, 65, which has a dimeater slightly smaller than the inside diameter of the second longitudinal bore 65.

The numeral 51 is a forming spatula portion being located in front of the handle portion 24 and having a shape like a dish. The numeral 52 is a wax melter, of which one end is mounted on the forming spatula portion 51. The other end of the wax melter 52 projects towards the extended axis along which the wax rod 8 slide down. The numeral 53 is a heater embedded in the wax melter 52.

The numeral 75 is a connecting tube made of metal having high strength such as stainless steel, which connects the handle portion 24 and the wax melter 52. The numeral 76 is a thermal insulator made of plastics. Lead wires (not shown in the drawings) are housed in the connecting tube 75 and the thermal insulator 76 to supply electric power to the heater 53. The lead wires are laid through the handle portion 24 and connected to the electric wire 5.

Figure 17:
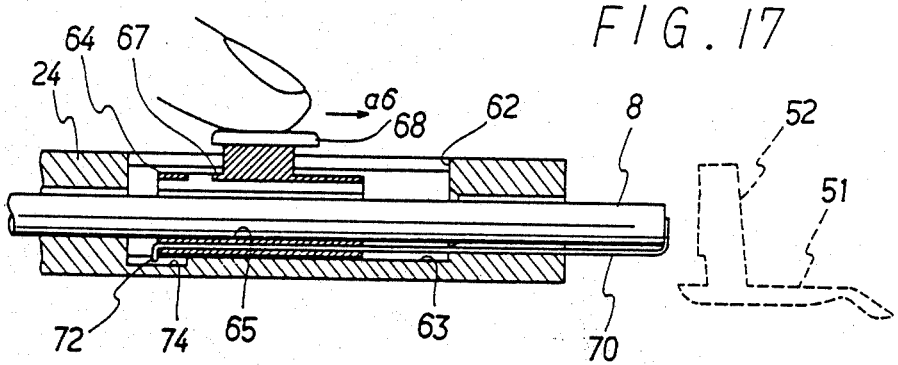
FIG. 17 is a partially sectional view of the sixth embodiment.

Next, there is explained the use of the tool in accordance with the sixth embodiment. The wax rod 8 is inserted into the first longitudinal bore 25 from the rear end, with the button 68 i.e. the inner tubular member 64 being in rear position as shown in FIG. 17. When the handle portion 24 is held in inclined or vertical posture with the rear end up, the wax rod 8 slides down by gravity through the second longitudinal bore 65 passing through the first longitudinal bore 25, until the front end thereof abuts against the stopper 54 to stop. At this moment the hooking means 72 of the stopper 70 is caught by the rear end of the inner tubular member 64 while the front end thereof is apart from the wax melter 52, and wax melting is not achieved. When the slidable button 68 is pressed to move the inner tubular member 64 forward in the direction of the arrow a6, the stopper 70 also proceeds due to the weight of the wax rod 8 to become in contact with the wax melter 52. Thus wax melting is commenced.

The distance of movement of the stopper 70 from the rearmost position thereof to the position in contact with the wax melter 52 is about 7-8 mm.

Molten wax flows down along the wax melter 52 and accumulates in the forming spatula portion 51. The wax rod 8 slides down by gravity according to the consumption, and the front end thereof is always received by the end of the stopper 70. A columnar weight having a diameter almost same as the wax rod 8 can be attached to the rear end of the wax rod 8 in order to help the sliding movement of the wax rod 8 by virtue of the weight.

When the required amount of molten wax is obtained in the forming spatula portion 51, the button 68 is moved backward. Thereby, the stopper 70 and the wax rod 8 are moved backward and the wax rod 8 is released from the wax melter 52. Molten wax accumulated in the forming spatula portion 51 is poured to the region to be wax-shaped and wax shaping work of artificial denture model is carried out.

Figure 18:
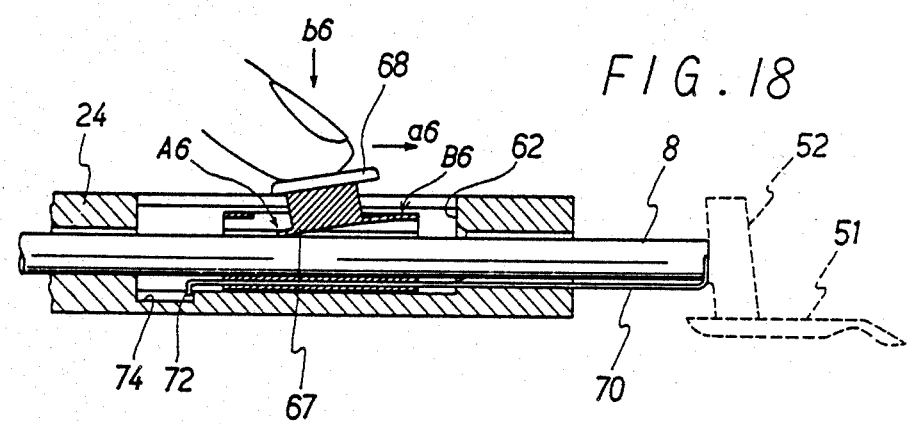
FIG. 18 is a partially sectional view of the sixth embodiment with the button being pressed.

In wax shaping work, when it is required to melt a lot of wax rapidly, the tool is operated as described below. The slidable button 68 is urged forward (in the direction of the arrow a6) with the button 68 being pressed down (the arrow b6) to urge the inner tubular member 64 forward in the condition that the stopper 70 is in contact with the wax melter 52 as shown in FIG. 18. Thereby, the wax rod 8, being nipped between the plate spring member 67 and the bottom of the second longitudinal bore 65 of the inner tubular member 64 is presses on the wax melter 52. Accordingly the wax melting rate is increased rapidly.

The distance of movement for pressing the max rod 8 on the wax melter 52 by force is about 7-8 mm.

After the above operation, when the button 68 and the inner tubular member 64 are moved backward with the button 68 being pushed down, the wax rod 8 is moved backward and the wax melting operation is ceased. When the button 68 is further moved backward, the rear end of the inner tubular member 64 catches the hooking means 72 provided at the rear end of the stopper 70 and the stopper 70 is moved back.

The retraction of the wax rod 8 also can be achieved with the button 68 being released from press. In this case, the stopper 70 moves backward soon after the button 68 moves.

In the above construction wherein the free end A6 of the plate spring member 67 is located on the rear side relative to a cantilever supporting part B6, when the wax rod 8 is pressed by means of the plate spring member 67 and is moved together with the inner tubular member 64, the pressing force acts in such direction that the plate spring member 67 slides on the surface of the wax rod 8. Namely, in the above arrangement the wax rod 8 is almost not scraped by the plate spring member 67, and therefore, there is less fear that the shavings of wax accumulate in the partially expanded bore 63.

The plate spring member 67 can be fitted with a thin rubber plate at the bottom surface in order to increase the friction resistance between the plate spring member 67 and the wax rod 8.

Figure 19:
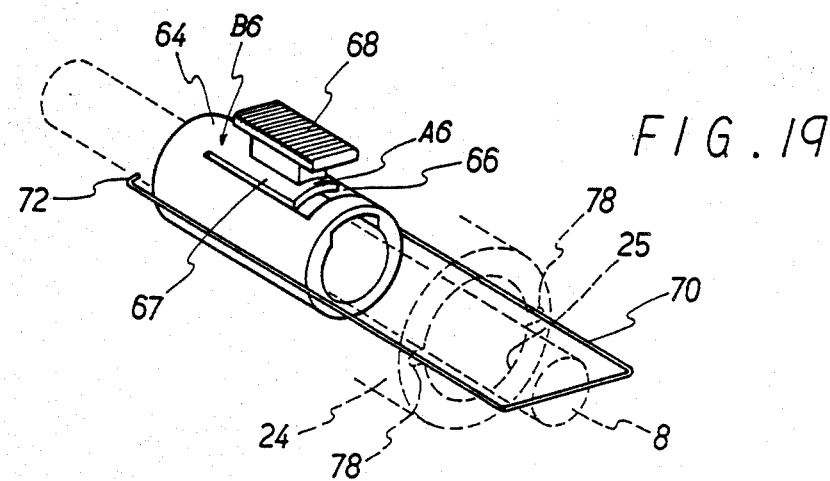
FIG. 19 is a perspective view showing an example of an altenative construction of an inner tubular member and a stopper.
Figure 20:
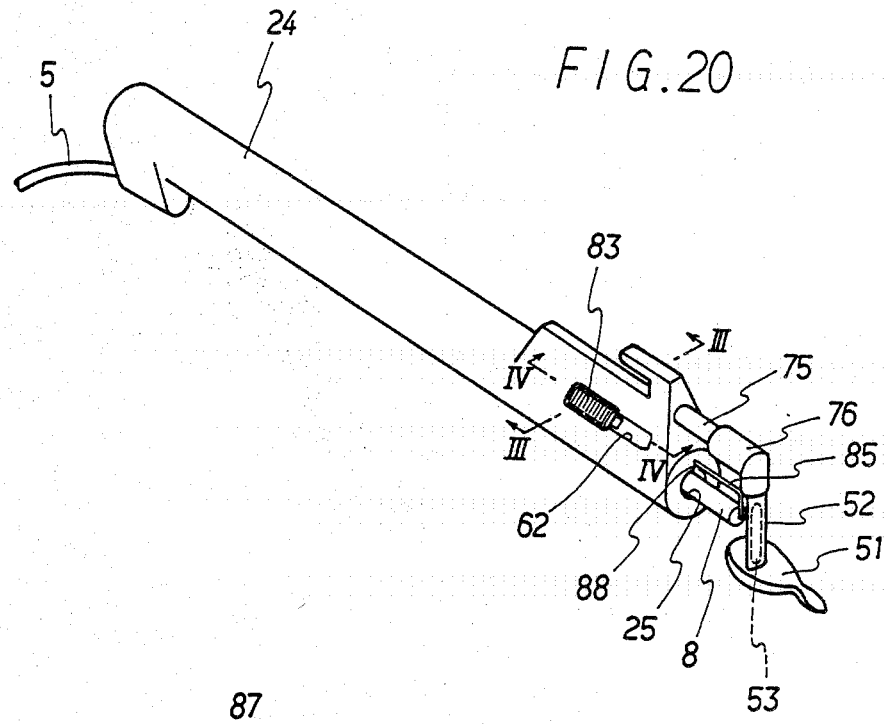
FIG. 20 is a perspective view of the seventh embodiment of a wax shaping tool in accordance with the present invention.
Figure 21:
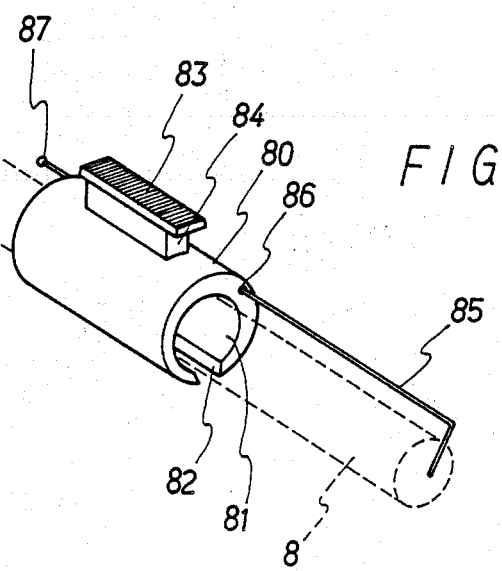
FIG. 21 is a perspective view of the inner tubular memer and the stopper of the seventh embodiment.

FIG. 19 shows an example of an alternative construction of the inner tubular member 64 and the stopper 70, wherein the free end A6 is provided in front of the cantilever supporting part B6. In addition, the stopper is formed in near U-shape and the hooking means 72 at the rear end is cranked inward which is to be caught by the rear end of the inner tubular member 64 for restriction of the movement. When this construction is employed and the wax rod 8 is pressed by means of the plate spring member 67 to be moved forward together with the inner tubular member 64, the plate spring member 67 cuts into the surface of the wax rod 8 and accordingly the proceeding force can be stronger than the previously mentioned example. Such a construction is effective when the wax rod 8 which has high hardness and can not easily scraped is moved forward by force.

The bottom surface of the plate spring member 67 can be fitted with a thin rubber plate like in the previous example. Thereby, the plate spring 67 contacts elasically the wax rod 8, and the amount of the generated shavings can be further decreased.

The stopper 70 is disposed outside of the inner tubular member 64 and is supported slidably forward and backward in the grooves 78 provided on the side walls of the first longitudinal bore 25 in the handle portion 24. The stopper 70 in this construction has the same function as that in the previous example in FIG. 13.

The stopper having U-shape can be effectively applied to the previous fifth embodiment also.

The seventh embodiment of the wax shaping tool in accordance with the present invention is illustrated in FIG. 20 to FIG. 25. In these drawings, the numeral 24 is a handle portion which has a long and slender shape like a rod and has concentrically a first longitudinal bore 25, being made of plastic material or the like. The first longitudinal bore 25 serves as a wax rod supporting means. The numeral 62 is an opening of the first longitudinal bore 25 provided near the front end of the handle portion 24. The numeral 63 is a partially expanded bore of the first longitudinal bore 25 provided at the location of the opening 62.

The numeral 79 represents a pair of ridges provided on the wall of the partially expanded bore 63. The numeral 80 is an inner tubular member housed in the partially expanded bore 63, having a second longitudinal bore 81 parallel to the longitudinal central axis of the handle portion 24 and having a longitudinal cutting 82. By the longitudinal cutting 82, the inner tubular member 80 reduces its inside diameter when it is pressed externally. The wall thickness of the inner tubular member 80 is the thinnest at the part adjacent to the longitudinal cutting 82 and the thickest at the opposite part. The inner tubular member 80 is supported by the ridge 79 in the partially expanded bore 63. The numeral 83 is a button provided at the location opposite to the longitudinal cutting 82 on the surface of the inner tubular member 80, and used for moving the inner tubular member 80 forward and backward and for pressing the same. The button 83 serves as a pressing means. The button 83 passes through the opening 62 and projects from the surface of the handle portion 24. The button 83 and a connecting member 84 can be formed integratedly together with the inner tubular member using the same material. The material can be resilient plastics such as polyacetal.

The numeral 85 is a stopper comprising a nearly L-shaped metal thread and having a hooking means 87 at the rear end thereof. The stopper 85 is supported slidably forward and backward in a small hole 86 provided in the inner tubular member 80, and pass through a groove 88 provided in the handle portion 24 to project forward from the handle portion 24.

The partially expanded bore 63 extends longer than the inner tubular member 80, and therefore, the inner tubular member 64 can be slided forward and backward within the partially expanded bore 63 when operated by the button 83. The numeral 8 is a wax rod inserted into both the first and the second longitudinal bore 25, 81, which has a diameter slightly smaller than the inside diameter of the first and the second longitudinal bore 25, 81.

Figure 22:
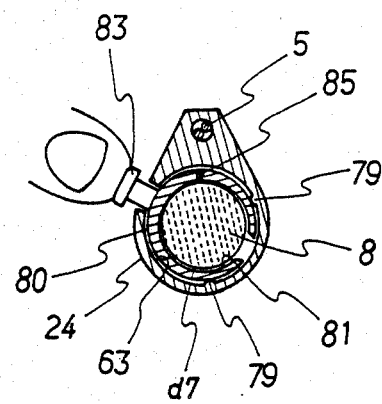
FIG. 22 is a sectional view taken along the plane III—III in FIG. 20 with the button being released.
Figure 23:
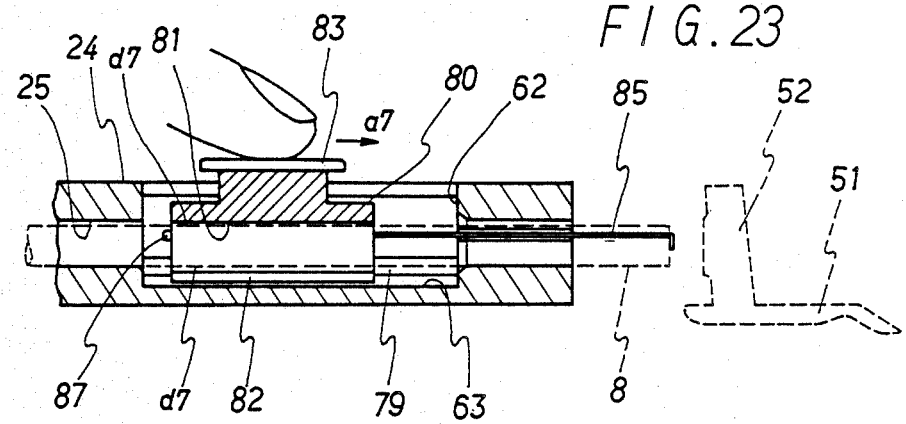
FIG. 23 is a sectional view taken along the plane IV—IV in FIG. 20 with the button being released.

As shown in FIG. 22 and FIG. 23, when the wax rod 8 is supported by the bottom of the first longitudinal bore 25, it is not contacted by the wall of the second longitudinal bore 81 of the inner tubular member 80. Namely, there is formed a uniform annular play $d_7$ between the wax rod 8 and the wall of the second longitudinal bore 81.

The inner tubular member 80 serves as a means for operating the stopper 85. The inner tubular member 80 and the button 83 organize a wax feed controller. Wherein, the inner tubular member corresponds to a first controlling means while the longitudinal cutting 82 of the inner tubular member 80 and the button 68 correspond to a second controlling means.

The numeral 51 is a forming spatula portion and the numeral 52 is a wax melter. The numeral 53 is a heater embedded in the wax melter 52. The numeral 75 is a connecting tube made of metal which connects the wax melter 52 with the handle portion 24. The numeral 76 is a thermal insulator made of plastics, and the numeral 5 represents electric wires.

Next, there is explained the use of the tool in accordance with the seventh embodiment. The wax rod 8 is inserted into the first longitudinal bore 25 from the rear end, with the button 83 (consequently the inner tubular member 80) being in rear position as shown in FIG. 22 and FIG. 23. When the handle portion 24 is held in inclined or vertical posture with the rear end up, the wax rod 8 slides down by gravity through the second longitudinal bore 81 and passes through the first longitudinal bore 25, until the front end thereof abuts against the stopper 85 to stop. At this moment, the hooking means 87 of the stopper 85 is caught by the rear end of the inner tubular member 80 while the front and thereof is apart from the wax melter 52, and wax melting is not achieved. When the button 83 is pressed to move the inner tubular member 80 forward in the direction of the arrow a7, the stopper 85 also proceeds due to the weight of the wax rod 8 to become in contact with the wax melter 52. Thus wax melting is commenced.

The distance of movement of the stopper 85 from the rearmost position thereof to the position in contact with the wax melter 52 is about 7-8 mm.

Molten wax flows down along the wax melter 52 and accumulates in the forming spatula portion 51. The wax rod 8 slides down by gravity according to the consumption, and the front end thereof is always received by the end of the stopper 85. A columnar weight having a diameter almost same as the wax rod 8 can be attached to the rear end of the wax rod 8 in order to help the sliding movement of the wax rod 8 by virtue of the weight.

When the required amount of molten wax is obtained in the forming spatula portion 51, the button 83 is moved backward. Thereby, the stopper 85 and the wax rod 8 is moved backward and the wax rod 8 is released from the wax melter 52. Molten wax accumulated in the forming spatula portion 51 is poured to the region to be wax-shaped and wax shaping work of artificial denture model is carried out.

Figure 24:
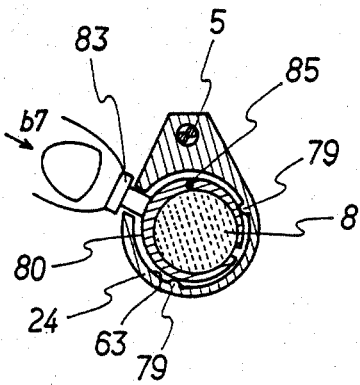
FIG. 24 is a sectional view taken along the plane III—III in FIG. 20 with the button being pressed.
Figure 25:
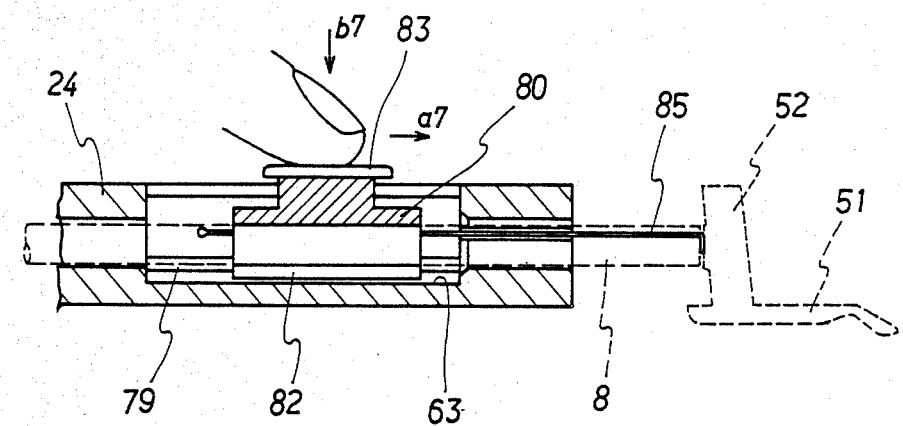
FIG. 25 is a sectional view taken along the plane IV—IV in FIG. 20 with the button being pressed.

In wax shaping work, when it is required to melt a lot of wax rapidly, the tool is operated as described below. The button 83 is urged forward (in the direction of the arrow a7) being pressed down (the arrow b7) to urge the inner tubular member 80 forward under the condition that the stopper 85 is in contact with the wax melter 52 as shown in FIG. 24 and FIG. 25. At this moment, the inside diameter of the inner tubular member 80 becomes smaller, and wax rod 8 is gripped by the uniform gripping force at the entire periphery.

Thereby, the wax rod 8 is urged forward together with the inner tubular member 80 and is pressed on the wax melter 52. Accordingly the wax melting rate is increased rapidly.

The distance of movement for pressing the wax rod 8 on the wax melter 52 by force is about 7-8 mm.

After the above operation, when the button 83 and the inner tubular member 80 are moved backward with the button 83 being pushed down, the wax rod 8 is moved backward and the wax melting operation is ceased. When the button 83 is further moved backward being released, the rear end of the inner tubular member 80 catches the hooking means 87 provided at the rear end of the stopper 85 and the stopper 85 is moved back.

The retraction of the wax rod 8 also can be achieved with the button 83 being released from pushing. In this case, the stopper 85 moves backward soon after the button 83 moves.

When the forced feed of wax rod 8 is required to be repeated many times, the inner tubular member 80 is moved backward with the wax rod 8 being released from the inner tubular member 80 by means of the operation of the button 83 after the completion of the first forced feed operation. Then the wax rod 8 is gripped again by the inner tubular member 80, which is achieved by means of pressing the button 83 again, and urged forward. By repeating this operation, a large amount of wax can be melted. In moving back the button 83 to prepare for the next forced feed, the wax rod 8 is not contacted by the wall of the second longitudinal bore 81 in the inner tubular member 80, and accordingly, the wax rod 8 is not moved back by the movement of the inner tubular member 80.

Figure 26:
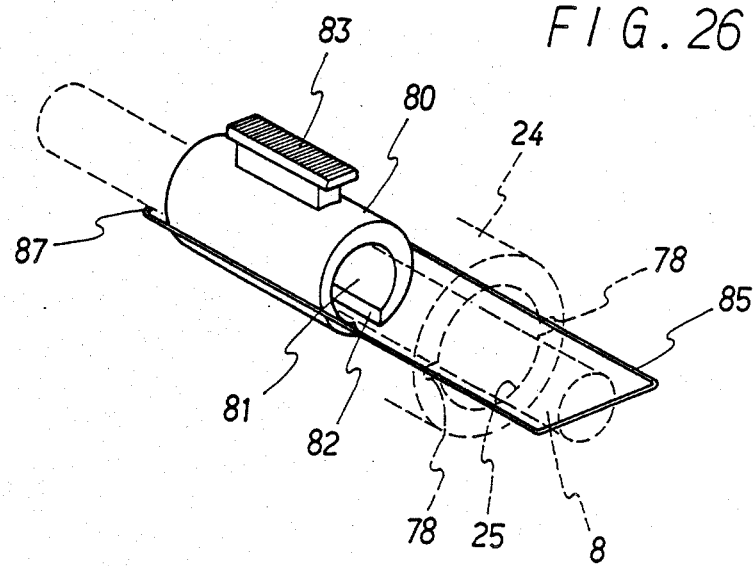
FIG. 26 is a perspective view showing another example of an alternative construction of an inner tubular member and a stopper.

FIG. 26 shows an example of an alternative construction of the inner tubular member 80 and the stopper 85, wherein the stopper 85 is formed in near U-shape and each hooking means 87 at the rear end is cranked inward which is to be caught by the rear end of the inner tubular member 80 for restriction of the movement.

The stopper 85 is disposed outside of the inner tubular means 80 and is supported slidably forward and backward in the grooves 78 provided on the side walls of the first longitudinal bore 25 in the handle portion 24. The stopper 85 in this construction has the same function as that in the previous example in FIG. 19.

Next, there is explained the structure of the forming spatula portion employed in the present invention.

A forming spatula portion having any construction described hereinafter can be employed in the first through the seventh embodiment as an alternative for each forming spatula portion of which the construction is explained in the description of each embodiment.

Figure 27:
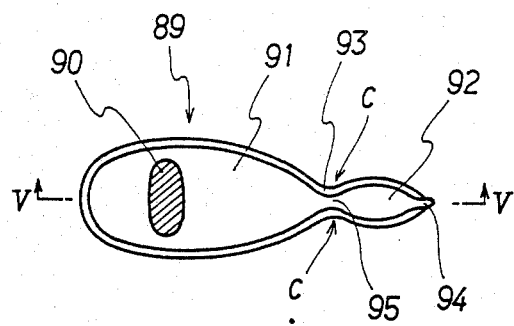
FIG. 27 is a plan view showing another example of a forming spatula portion.
Figure 28:
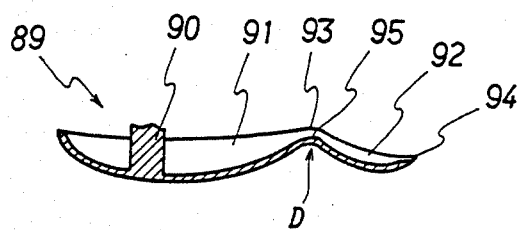
FIG. 28 is a sectional view taken along the plane V—V in FIG. 27.

In FIG. 27 and FIG. 28, the forming spatula portion 89 comprises a first reservoir 91, a second reservoir 92 and a bottleneck part 93 connecting with the first and the second reservoirs 91, 92. Molten wax which flows down along the wax melter 90 accumulates in the first reservoir 91 which has a shape like an elongated dish. The second reservoir 92 also has a shape like an elongated dish, and provided in front of the first reservoir 91 in downward inclined position relative to the first reservoir 91 at an angle of about 15 to 20 degrees.

The first reservoir 91 has a capacity to hold the amount of wax required for a series (about 3 to 5 times) of wax shaping operations, and the second reservoir 92 as a capacity to hold the amount of wax usually requried for one wax shaping operation. The required amount for an actual wax shaping work differs depending on size, shape and the like of the tooth. However, the adequate capacity of the first reservoir 91 is about 0.05 to 0.1 cc, and the adequate capacity of the second reservoir 92 is about 0.01 to 0.04 cc.

The numeral 94 is a narrow ditch formed at the front end of the second reservoir 92 and is opened at the front edge. Through the narow ditch 94, wax is poured to the region to be wax-formed in such a manner that points or lines are drawn on the above region.

The numeral 95 is a passage formed at the bottleneck part 93, through which molten wax accumulated in the first reservoir 91 is transfered to the second reservoir 92. The bottleneck part 93 is narrow horizontally and shallow vertically, and is elevated relative to the other parts, and the passage 95 is also elevated. Therefore, it is required for the first reservoir 91 to be inclined forward at a relatively steep angle in order to allow the accumulated wax in the first reservoir 91 to flow into the second reservoir 92. The side walls C and the bottom D of the bottleneck part 93 can be seen in FIG. 27 and FIG. 28 respectively.

Using the above mentioned construction, wax melting is achieved by means of bringing the front end of the wax rod 8 into contact with the heated wax melter 90. Thereby, molten wax flows down along the wax melter 90 and accumulates in the first reservoir 91 of the forming spatula portion 89. The amount of molten wax is controlled by the duration time of contact of the wax rod 8 and the wax melter 90. The duration time is selected at the discretion of the dental technician considering the conditions of the wax shaping work.

Figure 29:
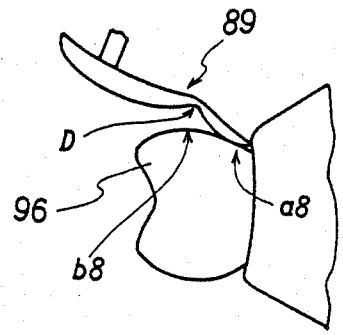
FIG. 29 is a side view showing a sight of wax shaping work.

During the wax shaping work, molten wax of required amount being accumulated in the second reservoir 92 of the forming spatula portion 89 is poured to periphery of crown, occlusal surface, cusp or the like. In case of shaping a periphery a of dental cervix a8 of an artificial denture model 96 as illustrated in FIG. 29, the work is carried out in such a manner that poured wax is smoothed by the bottom surface of the second reservoir 92. At this moment, there is less possibility that other part in the forming spatula portion 89 contacts a convex part b8 by virtue of the elevated bottom D of the bottleneck part 95. Therefore, there is quite less fear that the other part in the forming spatula portion 89 contacts the wax on the convex part b8 which has been finished in wax shaping and melts to deform it.

Figure 30:
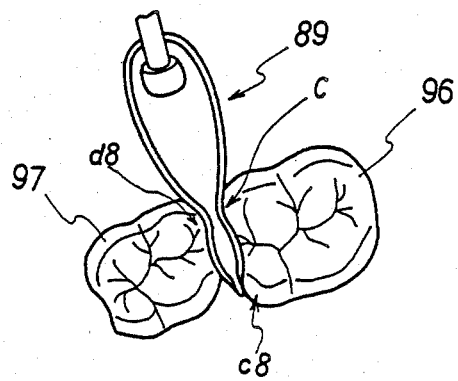
FIG. 30 is a plan view showing another sight of wax shaping work.

Further, in case of shaping a periphery c8 of an embrassure of an artificial dentition model 96 as illustrated in FIG. 30, there is less possibility of fear that other part in the forming spatula portion 89 contacts an angle portion d8 of the adjacent tooth by virtue of the elevated bottom D of the bottleneck part 95.

To employ the above construction of the forming spatula portion is effective as described below.

First, the forming spatula portion is devided into a first reservoir and a second reservoir, and the both reservoirs are communicated by a bottleneck part. The required amount of wax for plural wax shaping operations is accumulated in the first reservoir and the required amount of wax for one wax shaping operation is accumulated in the second reservoir. Therefore the required wax amount for one wax shaping operation can be confirmed when wax is poured to the region to be wax-shaped. To employ this construction enables delicate wax shaping work on cusp or other delicate work, for example, building up wax on a spot, drawing a line and the like.

Next, since the required amount of wax for several times of shaping operations are melted and accumulated in the first reservoir just before the operation, there is no problem of decomposition or degradation of wax.

Thirdly, a bottleneck part is provided between the first reservoir and the second reservoir. By virtue of the construction provided on the side walls and on the bottom, the wax shaping operation becomes easier. The artifical denture model has many convex parts and concave parts complicatedly, and therefore, the bottom surface of the forming spatula portion is apt to contact to melt the wax on the other part than the region under operation. However, by employing the above construction, the possibility of such undesirable contacts can be lowered considerably.

Figure 31:
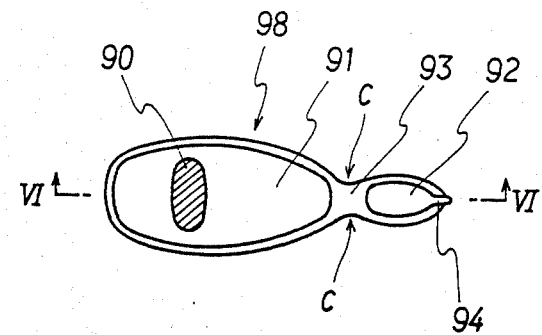
FIG. 31 is a plan view showing further example of a forming spatula portion.
Figure 32:
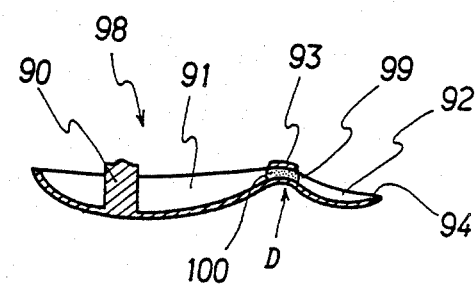
FIG. 32 is a sectional view taken along the plane VI—VI in FIG. 31.

FIG. 31 and FIG. 32 show further example of a construction of the forming spatula portion 98. A forming spatula portion in accordance with this example has a construction almost similar to the former example in FIG. 27 and FIG. 28 unless otherwise described hereinafter.

The forming spatula portion 98 comprises a first reservoir 91, a second reservoir 92 and a bottleneck part 93 connecting the first and the second reservoirs 91, 92. Molten wax which flows down along the wax melter 90 accumulates in the first reservoir 91 which has a shape like an elongated dish. The second reservoir 92 also has a shape like an elongated dish, and provided in front of the first reservoir 91 in downward inclined position relative to the first reservoir 91 at an angle of about 15 to 20 degrees. At the bottleneck part 93, there is formed an orifice 99 having an inside diameter of 0.3 to 1.0 mm through which the first reservoir 91 can communicates with the second reservoir 92.

Capacities of the first and the second reservoirs and the other construction of this example are same as those of the former example.

The orifice 99 can be filled with a wax restricting material 100 such as cotton, felt, sponge, or the like. To fill the restricting material 100 is effective particularly when the orifice 99 has a large diameter.

When the forming spatula portion 98 is titled in a manner that the front end thereof is lowered, the molten wax accumulated in the first reservoir 91 flows through the orifice 99 of the bottleneck part 93 to the second reservoir 92.

Figure 33:
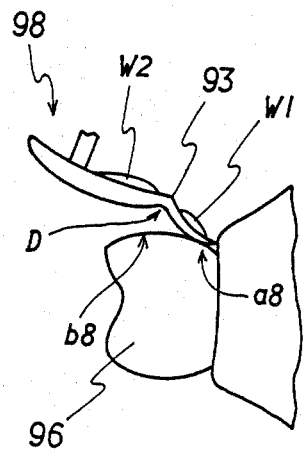
FIG. 33 is a side view showing further sight of wax shaping work.

When the forming spatula portion 98 is inclined as shown in the FIG. 33, the amount of the molten wax $W_1$ accumulated in the second reservoir 92 is at the maximum volume held therein assisted by the surface tension of the molten wax and the surface swells. At this moment, the molten wax $W_2$ accumulated in the first reservoir 91 is ready for flowing toward the bottleneck part 93 and swells slightly due to the surface tension.

Under such a condition as mentioned above, when a narrow ditch 94 at the front end of the second reservoir 92 is put to the region to be wax-formed or moved there, wax shaping is carried out in a form of spot or line. Make-up of molten wax to the second reservoir 92 is carried out automatically from the first reservoir 91 through the orifice 99 in such a manner that the second reservoir 92 is re-filled with the equal amount of molten wax to the consumption due to pouring to the region to be wax-shaped. Therefore, by keeping the forming spatula portion 98 in a nearly constant inclined posture, the amount of molten wax held in the second reservoir 92 with the assistance of the surface tension can be maintained without large change.

As mentioned above, the forming spatula portion 98 of the example in FIG. 31 and FIG. 32 has a construction wherein the first reservoir 91 and the second reservoir 92 is segregated by the bottleneck part 93, and molten wax flows from the first reservoir 91 into the second reservoir 92 through the orifice 99 in the bottleneck part 93. Therefore, the amount of molten wax in the reservoir 92 is kept constantly by virtue of the surface tension, and the amount corresponding to the consumption is re-filed through the orifice 99. Further in the first reservoir 91 also, the accumulated wax is kept in swelled form due to the surface tension, because the flowing out thereof is restricted at the bottleneck part 93. Thereby, flow of wax from the first reservoir 91 to the second reservoir 92 is controlled so that excess flow can be prevented, and therefore, pouring molten wax from the front end of the second reservoir can be carried out 92 moderately like writing a letter with a fountain pen.

What is claimed is:

1. A wax shaping tool comprising:
    a handle portion suitable for holding in a hand;
    a means for supporting wax rod, which is fixed to the handle portion and has a stopper at the front end thereof, wherein a wax rod is supported slidably downward by gravity and stops with the front end thereof abutting against the stopper;
    a forming spatula portion made of metalic material and fixed to the front side of the handle portion, which can hold up molten wax and also has a function to flow wax to the region for shaping and to build up and shape wax;
    a wax melter made of metalic material and provided on and connected to the forming spatula portion, which can melt the wax rod at contacting surface;
    a heater which heats up the forming spatula portion and the wax melter;
    a wax feed controller which makes the front end of the wax rod and the wax melter in contacted condition or in released condition, where in contacted condition the wax rod is melted from the front edge then continues to be melted due to sliding down of wax rod by gravity and molten wax accumulates in the forming spatula portion, while in released condition the wax rod stops being melted.

2. The tool of claim 1, wherein the wax rod supporting means is supported by the handle portion, the front end thereof is located close to the wax melter and the rear end thereof is extended upward in inclined posture.

3. The tool of claim 2, wherein the wax melter has a substantially columnar shape with the lower end being supported pivotably by the forming spatula portion and with the upper end being free; the wax feed controller comprises a means for operating the wax melter being provided on the handle portion, of which the forward movement makes the wax melter rotate in one direction to contact the end of the wax rod while the backward movement makes the wax melter rotate in the other direction to part from the end of the wax rod; and the heater is formed on the forming spatula portion.

4. The tool of claim 3, wherein the forming spatula portion comprises:
    a first reservoir having a shape substantially like a dish capable to hold wax in the required amount for plural times of wax shaping operations and being arranged horizontally;
    a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
    a bottleneck passage communicating with the first reservoir and the second reservoir, allowing wax to flow from the first reservoir to the second reservoir and being constricted at side walls and at the bottom.

5. The tool of claim 4, wherein the bottleneck passage comprises a groove.

6. The tool of claim 4, wherein the bottleneck passage comprises an orifice.

7. The tool of claim 6, wherein the orifice is filled with wax restricting material which restrains the rate of wax flow from the first reservoir to the second reservoir.

8. The tool of claim 2, wherein the wax feed controller comprises a means for operating the wax rod supporting means which is formed at connecting part of the wax rod supporting means and the handle portion and can move the wax rod supporting means forward and backward wherein moving forward of the wax rod supporting means brings the end of wax rod in contact with the wax melter while moving backward makes the end of wax rod apart from the wax melter, and the heater is embedded in the wax melter.

9. The tool of claim 8, wherein the forming spatula portion comprises:
  a first reservoir having a shape substantially like a dish capable to hold wax in the required amount for plural times of wax shaping operations and being arranged horizontally;
  a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
  a bottle neck passage communicating with the first reservoir and the second reservoir, allowing wax to flow from the first reservoir to the second reservoir and being constricted at side walls and at the bottom.

10. The tool of claim 9, wherein the bottle neckpassage comprises a groove.

11. The tool of claim 9, wherein the bottle neck passage comprises an orifice.

12. The tool of claim 11, wherein the orifice is filled with wax restricting material which restrains the rate of wax flow from the first reservoir to the second reservoir.

13. The tool of claim 1, wherein the wax rod supporting means comprises a first longitudinal bore, and the stopper is supported by the handle portion with the end thereof being located between the end of handle portion and the wax melter.

14. The tool of claim 13, wherein the wax melter has a substantially columnar shape with the lower end being supported pivotably by the forming spatula portion; the wax feed controller comprises a means for operating the wax melter capable of rotating the wax melter, being provided on the handle portion, of which the forward movement makes the wax melter rotate in one direction to contact the end of the wax rod while the backward movement makes the wax melter rotate in the other direction to part from the end of the wax rod; and the heater is embedded in the forming spatula portion.

15. The tool of claim 14, wherein the forming spatula portion comprises:
  a first reservoir having a shape substantially like a dish capable to hold wax in the required amount for plural times of wax shaping operations and being arranged horizontally;
  a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
  a bottle neck passage communicating with the first reservoir and the second reservoir, allowing wax to flow from the first reservoir to the second reservoir and being constricted at side walls and at the bottom.

16. The tool of claim 15, wherein the bottleneck passage comprises a groove.

17. The tool of claim 15, wherein the bottleneck passage comprises an orifice.

18. The tool of claim 17, wherein the orifice is filled with wax restricting material which restrains the rate of wax flow from the first reservoir to the second reservoir.

19. The tool of claim 13, wherein the wax feed controller comprises a means for operating the stopper which is formed at the handle portion and can move the stopper forward and backward wherein moving forward of the stopper brings the stopper and the end of wax rod in contact with the wax melter while moving backward makes the stopper and the end of wax rod apart from the wax melter, and the heater is embedded in the wax melter.

20. The tool of claim 19, wherein the stopper comprises an L-shaped metal thread.

21. The tool of claim 19, wherein the forming spatula portion comprises:
  a first reservoir having a shape substantially like a dish capable to hold wax in the required amount for plural times of wax shaping operations and being arranged horizontally;
  a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
  a bottle neck passage communicating with the first reservoir and the second reservoir, allowing wax to flow from the first reservoir to the second reservoir and being constricted at side walls and at the bottom.

22. The tool of claim 21, wherein the bottleneck passage comprises a groove.

23. The tool of claim 21, wherein the bottleneck passage comprises an orifice.

24. The tool of claim 23, wherein the orifice is filled with the wax restricting material which restrains the rate of wax flow from the first reservoir to the second reservoir.

25. A wax shaping tool comprising:
  a handle portion suitable for holding in a hand;
  a means for supporting wax rod comprising first longitudinal bore formed in the handle portion, wherein a wax rod is inserted into the first longitudinal bore and supported slidably downward by gravity;
  a forming spatula portion made of metalic material and fixed to the front side of the handle portion, which can hold up molten wax and also has a function to flow wax to the region for shaping and to build up and shape wax;
  a wax melter made of metalic material and provided on and connected to the forming spatula portion, which can melt the wax rod at contacting surface;
  a heater which heats up the forming spatula portion and the wax melter;
  a stopper supported by the handle portion, of which the front end is disposed between the front end for the handle portion and wax melter, wherein the wax rod inserted in the first longitudinal bore stops with the front end of the wax rod abutting against the front end thereof; and a wax feed controller which makes the front end of the wax rod and the wax melter in contacted condition or in released condition, where in contacted condition the wax rod is melted from the front end and molten wax accumulates in the forming spatula portion, while in released condition the wax rod stops to be melted, the wax feed controller comprising a first controlling means comprising a means for operating the stopper, which is provided at the handle portion and moves the stopper to a forward position or to a rear position, where in the forward position the stopper contacts the wax melter to allow the wax rod to be melted from the front end and to be continuously melted due to sliding down of the wax rod by gravity and molten wax accumulates in the forming spatula portion, while in the rear position the stopper parts from the wax melter and the front end of wax rod also parts therefrom; and a second controlling means which can force wax rod to proceed forward and can press the front end of the wax rod against the wax melter when the stopper is in the forward portion.

26. The tool of claim 25, wherein the first controlling means comprises an inner tubular member housed slidably forward and backward in a first longitudinal bore, which has a second longitudinal bore for passing through of wax rod and catches the rear end of the stopper to control the forward movement of the stopper; and the second controlling means comprises a pressing member mounted on the inner tubular member, of which the bottom surface faces the second longitudinal bore, being urged elastically outward by a spring means wherein to press the pressing member makes the bottom surface project into the second longitudinal bore to nip wax rod between the bottom surface and the wall of the second longitudinal bore, thereby the forward movement of the inner tubular member forces wax rod to proceed and presses the end of wax rod on the wax melter.

27. The tool of claim 26, wherein the heater is embedded in the wax melter and the forming spatula portion comprises:
a first reservoir having a shape substantially like a dish capable to hold wax in the required amount for plural times of wax shaping operations and being arranged horizontally;
a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
a bottle neck passage communicating with the first reservoir and the second reservoir, allowing wax to flow from the first reservoir to the second reservoir and being constricted at side walls and at the bottom.

28. The tool of claim 27, wherein the bottleneck passage comprises a groove.

29. The tool of claim 27, wherein the bottleneck passage comprises an orifice.

30. The tool of claim 29, wherein the orifice is filled with wax restricting material which restrains the rate of wax flow from the first reservoir to the second reservoir.

31. The tool of claim 26, wherein the stopper comprises nearly L-shaped metal thread, being supported slidably forward and backward in a small hole formed in a wall of the inner tubular member, and has a hooking means at the rear end to be caught by the end of inner tubular member.

32. The tool of claim 26, wherein the stopper comprises nearly U-shaped metal thread, being supported slidably forward and backward in grooves formed in a wall of the first longitudinal bore of the handle portion, and has a hooking means at the rear end to be caught by the end of the inner tubular member.

33. The tool of claim 25, wherein the first controlling means comprises an inner tubular member housed slidably forward and backward in a first longitudinal bore, which has a second longitudinal bore for passing through of wax rod and catches the rear end of the stopper to control the forward movement of the stopper; and the second controlling means comprises plate spring member formed on the inner tubular member with nearly U-shaped cutting and a pressing means to press the plate spring member wherein to press the pressing means makes the plate spring member bow downward to project into the second longitudinal bore to nip wax rod between the plate spring member and the wall of the second longitudinal bore, thereby, the forward movement of the inner tubular member forces wax rod to proceed and presses the end of wax rod on the wax melter.

34. The tool of claim 33, wherein the heater is embedded in the wax melter and the forming spatula portion comprises:
a first reservoir having a shape substantially like a dish capable to hold wax in the required amount for plural times of wax shaping operations and being arranged horizontally;
a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir; and
a bottleneck passage communicating with the first reservoir and the second reservoir, allowing wax to flow from the first reservoir to the second reservoir and being constricted at side walls and at the bottom.

35. The tool of claim 34, wherein the bottleneck passage comprises a groove.

36. The tool of claim 34, wherein the bottleneck passage comprises an orifice.

37. The tool of claim 36, wherein the orifice is filled with wax restricting material which restrains the rate of wax flow from the first reservoir to the second reservoir.

38. The tool of claim 33, wherein the stopper comprises nearly L-shaped metal thread, being supported slidably forward and backward in a small hole formed in a wall of the inner tubular member, and has a hooking means at the rear end to be caught by the end of inner tubular member.

39. The tool of claim 33, wherein the stopper comprises nearly U-shaped metal thread, being supported slidably forward and backward in grooves formed in a wall of the first longitudinal bore of the handle portion, and has a hooking means at the rear end to be caught by the end of the inner tubular member.

40. The tool of claim 33, wherein the free end of the plate spring member is disposed on the rear side relative to the cantilever supporting part.

41. The tool of claim 33, wherein the free end of the plate spring member is disposed in front of the cantilever supporting part.

42. The tool of claim 25, wherein the first controlling means comprises an inner tubular member housed slidably forward and backward in a first longitudinal bore, which has a second longitudinal bore for passing through of wax rod and catches the rear end of the stopper to control the forward movement of the stopper; and second controlling means comprises a longitudinal cutting on the inner tubular member and a pressing means located on the opposite side to the longitudinal cutting of the inner tubular member wherein to press the pressing means makes the inside diameter of the inner tubular member decrease by narrowing the longitudinal cutting to hold wax rod, thereby the forward movement of the inner tubular member forces wax rod to proceed and presses the end of wax rod on the wax melter.

43. The tool of claim 42, wherein the forming spatula portion comprises a first reservoir having a shape substantially like a dish capable to hold wax in the required amount for plural times of wax shaping operations and being arranged horizontally;

a second reservoir having a shape substantially like an elongated dish capable to hold wax in the required amount for one wax operation, being provided with a narrow ditch at the front end which opens at the forward end, extending from the front end of the first reservoir and being inclined downward relative to the first reservoir;

and a bottleneck passage communicating with the first reservoir and the second reservoir, allowing wax to flow from the first reservoir to the second reservoir and being constricted at side walls and at the bottom.

44. The tool of claim 43, wherein the bottleneck passage comprises a groove.

45. The tool of claim 43, wherein the bottleneck passage comprises an orifice.

46. The tool of claim 45, wherein the orifice is filled with wax restricting material which restrains the rate of wax flow from the first reservoir to the second reservoir.

47. The tool of claim 42, wherein the stopper comprises nearly L-shaped metal thread, being supported slidably forward and backward in a small hole formed in a wall of the inner tubular member, and has a hooking means at the rear end to be caught by the end of inner tubular member.

48. The tool of claim 42, wherein the stopper comprises nearly U-shaped metal thread, being supported slidably forward and backward in grooves formed in a wall of the first longitudinal bore of the handle portion, and has a hooking means at the rear end to be caught by the end of the inner tubular member.

* * * * *